United States Patent
Kwang et al.

(10) Patent No.: US 9,826,773 B2
(45) Date of Patent: Nov. 28, 2017

(54) BRAZZEN MULTIPLE VARIANTS OF INCREASED SWEETNESS, AND PRODUCTION METHOD FOR SAME

(71) Applicant: CHUNG-ANG UNIVERSITY INDUSTRY—ACADEMIC COOPERATION FOUNDATION [KR/KR], Seoul (KR)

(72) Inventors: Kong Hoon Kwang, Incheon (KR); Hyeondong Do, Daejeon (KR)

(73) Assignee: BIOSWEET CO., LTD., Seoul (KR)

( * ) Notice: Subject to any disclaimer, the term of this patent is extended or adjusted under 35 U.S.C. 154(b) by 370 days.

(21) Appl. No.: 14/418,719

(22) PCT Filed: Feb. 1, 2013

(86) PCT No.: PCT/KR2013/000840
§ 371 (c)(1),
(2) Date: Jan. 30, 2015

(87) PCT Pub. No.: WO2014/021526
PCT Pub. Date: Feb. 6, 2014

(65) Prior Publication Data
US 2017/0143024 A1    May 25, 2017

(30) Foreign Application Priority Data
Jul. 30, 2012  (KR) ......................... 10-2012-0083473

(51) Int. Cl.
| | |
|---|---|
| C12P 21/06 | (2006.01) |
| C12N 15/00 | (2006.01) |
| C12N 5/00 | (2006.01) |
| C07H 21/04 | (2006.01) |
| C07K 14/00 | (2006.01) |
| A23L 33/10 | (2016.01) |
| C07K 14/43 | (2006.01) |
| A23J 3/14 | (2006.01) |

(52) U.S. Cl.
CPC ................. *A23L 33/10* (2016.08); *A23J 3/14* (2013.01); *C07K 14/43* (2013.01); *A23V 2002/00* (2013.01)

(58) Field of Classification Search
None
See application file for complete search history.

(56) References Cited

U.S. PATENT DOCUMENTS

| | | |
|---|---|---|
| 6,274,707 B1 | 8/2001 | Markley et al. |
| 8,592,181 B2 | 11/2013 | Kong |
| 2004/0018290 A1 | 1/2004 | Jin et al. |
| 2008/0281077 A1 | 11/2008 | Assadi-Porter |

FOREIGN PATENT DOCUMENTS

| | | |
|---|---|---|
| KR | 10-2009-0050525 A | 10/2010 |
| KR | 10-2010-0097042 A | 11/2011 |
| WO | WO-99-25835 A1 | 5/1999 |
| WO | WO-2011-025077 A1 | 3/2011 |
| WO | WO-2011-105841 A9 | 9/2011 |

OTHER PUBLICATIONS

Assadi-Porter et al., "Sweetness determinant sites of brazzein, a small, heat-stable, sweet-tasting protein." Arch Biochem Biophys, 376(2):259-65 (2000)—Abstract only.
Do, Hyeondong, "Studies on Functions of Brazzein, Sweet-Tasting Protein by site-direction mutagenesis," (2012), 37 pages—(w/English abstract)
Graham, F.L. et al., "A New Technique for the Assay of Infectivity of Human Adenovirus 5 DNA", Virology 52, 456-467 (1973).
Hanahan Douglas, "Studies on Transformation of *Escherichia coli* with Plasmids", J. Mol. Biol., 166, 557-580, (1983).
Hellekant Goran et al., "Critical regions for the sweetness of Brazzein", FEBS Letters., 544; 33-37 (2003).
Hellekant Goran. et al., Brazzein a Small, Sweet Protein: Discovery and Physiological Overview, Chem. Senses., 30;88-89, (2005).
Jin Zheyuan et al., "Monkey Electrophysiological and Human Psychophysical Responses to Mutants of the Sweet Protein Brazzein: Delineating Brazzein Sweetness", *Chem. Senses*, 28;491-498, (2003).
Kaneko Ryosuke et al., "Structure—Sweetness relationship in Thaumatin: Importance of Lysine Residues" Chem. Senses, 26; 167-177, (2001).
Kitabatake Naofumi et al., "Developments in Biotechnological Production of Sweet Proteins", Journal of Bioscience and Bioengineering, 102(5), 375-389 (2006).
Lee, J. J. et al., "Design and Efficient Soluble Expression of a Sweet Protein, Brazzein and Minor-Form Mutant," Bull. Korean Chem. Soc. 31(12):3830-3833 (2010).
Liu Xiaozhu et al., "Purification, complete amino acid sequence and structural characterization of the heat-stable sweet protein, mabinlin II" Eur. J. Biochem., 67;281-287 (1993).
Magnuson A. et al., "Aspartame: A Safety Evaluation Based on Current Use Levels, Regulations, and Toxicological and Epidemiological Studies" Critical Reviews in Toxicology, 37:629-727 ( 2007).
Ming Ding et al., "Brazzein, a new high-potency thermostable sweet protein from Pentadiplandra brazzeana B." FEBS Letters, 355, 106-108 (1994).
Moris, James et al., "Purification of Monellin, The Sweet Principle of Dioscoreophyllum Cumminsii" Biochim. Biophys. Acta 26; 114-122 (1972).
Nelson, Greg, et al., "Mammalian Sweet Taste Receptors," Cell Press 106:381-390 (2001).
Neumann, E. et al., "Gene transfer into mouse lyoma cells by electroporation in high electric fields" EMBO J., 1841(1982).
Nirasawa, Satoru et al., "Structures of heat-stable and unstable homologues of the sweet protein mabinlin. The difference in the heat stability is due to replacement of a single amino acid residue", Eur. J. Biochem. 223; 989-995 (1994).
Raina et al., "Making and breaking Disulfide Bonds", Ann. Rev. Microbiol, 51;179-202, (1997).
Rietsch Arne, "An in vivo pathway for disulfide bond isomerization in *Escherichia coli*", Proc. Natl. Acad. Sci. 93; 13048-13053, (1996).
Schagger Hermann et al., "Tricine-Sodium Dodecyl Sulfate-Polyacrylamide Gel Electrophoresis for the Separation of Proteins in the Range from 1 to 100 kDa", Analytical Biochemistry 166; 368-379, (1987).

(Continued)

*Primary Examiner* — Catherine S Hibbert
(74) *Attorney, Agent, or Firm* — IPLA P.A.; James E. Bame

(57) ABSTRACT

The present invention relates to novel brazzein multiple variants having increased sweetness, and a production method for the same.

6 Claims, 15 Drawing Sheets

(56) References Cited

OTHER PUBLICATIONS

Snyder William et al., "b-Galactosidase Is Inactivated by Intermolecular Disulfide Bonds and Is Toxic when Secreted to the Periplasm of *Escherichia coli*" Journal of Bacteriology, p. 953-963, (1995).

Sone Michio et al., "Differential in Vivo Roles Played by DsbA and DsbC in the Formation of Protein Disulfide Bonds" The Journal of Biological Chemistr vol. 272, No. 16, pp. 10349-10352, (1997).

Sung, Yoon-Hui, "Solution Structure, Backbone Dynamics, and Stability of a Double Mutant Single-chain Monellin" The Journal of Biological Chemistry, 276, 22; 19624-19630 (2001).

Suzuki Maiko et al., "Recombinant curculin heterodimer exhibits taste-modifying and sweet-tasting activities", FEBS Letters, 573; 135-138 (2004).

Tancredi Teodorico et al., "Interaction of sweet proteins with their receptor" Eur. J. Biochem. 271; 2231-2240 (2004).

Temussi Andrea, "Why are sweet proteins sweet? Interaction of brazzein, monellin and thaumatin with the T1R2-T1R3 receptor", FEBS Letters 526; 1-4, (2002).

Theeraslip Sarroch et al., "Complete Purification and Characterizatioonf the Taste-modifying Protein, Miraculin, from Miracle Fruit", The Journal of Biological Chemistry, 263, 23; 11536-11539 (1988).

Uhlmann Eugen et al., "Antisense Oligonucleotides: A New Therapeutic Principle", Chemical Reviews 90, 4; 543-584 (1990).

Van Der Wel Henrik et al., "Isolation and Characterization of Thaumatin I and II, the Sweet-Tasting Proteins from Thaumatococcus danielliii Benth" Eur. J. Biochem. 31,221-225 (1972).

Walters Eric et al., "Interactions of the Sweet Protein Brazzein with the Sweet Taste Receptor", Journal of Agricultural and Food Chemisrt, 54; 10129-10133 (2006).

Walters, et al., "Design and Evaluation of New Analogs of the Sweet Protein Brazzein," Chem. Senses 34:679-683 (2009).

Wong Tao-Kin et al., "Appearance of B-lactamase activity in animal cells upon liposome-mediated gene transfer", Gene, 10; 87-94 (1980).

Yamashita Haruyuki et al., "Purification and Complet Amino Acid Sequence of a New Type of Sweet Protein with Tas-modifying Activity, Curculin" The Journal of Biological. Chemistry, vol. 265, No. 26, pp. 15770-15775 (1990).

Yanofsky Charles et al., "Repression Is Relieved I3efore Attenuation in the trp Operon of *Escherichia coli* as Tryptophan Starvation Becomes Increasingly Severe" Journal of Bacteriology, p. 1018-1024 vol. 158, No. 3 (Jun. 1984).

Yoon, Sug-Young, et al., "Residue mutations in the sweetness loops for the sweet-tasting protein brazzein," Food Chemistry 129:1327-1330 (2011).

ён
BRAZZEIN MULTIPLE VARIANTS OF INCREASED SWEETNESS, AND PRODUCTION METHOD FOR SAME

INCORPORATION-BY-REFERENCE OF SEQUENCE LISTING

The contents of the text file named "DAPA006N01US_SeqList.txt", which was created on Apr. 22, 2015, and is 14 kilobytes in size, are hereby incorporated by referenced in their entirety.

CROSS-REFERENCE TO RELATED APPLICATIONS

This application is a national stage application, filed under 35 U.S.C. §371, of International Application No. PCT/KR2013/00840, filed on Feb. 1, 2013, which claims priority to, and the benefit of, Korean Patent Application No. 10-2012-0083473, filed Jul. 30, 2012. The contents of each application are incorporated by reference in their entirety.

BACKGROUND

1. Field of the Invention

The present invention relates to a novel brazzein multiple variants having increased sweetness, and a production method for the same.

2. Discussion of Related Art

White sugar (refined sugar) is a type of saccharide, and more specifically, is a disaccharide referred to as a kind of saccharose (a chemical term referring to sugar) composed of a simple carbohydrate called "sucrose". Sugar has been frequently used as a sweetener for a long period of time. However, the World Health Organization (WHO) has proposed a recommendation to limit the consumption of sugar to 10% of the current level because of health problems caused by sugar, and state governments of the United States have prohibited in selling foods including sugar as a major ingredient and beverages including a high content of sugar. Further, in Korea, the National Obesity Taskforce has been organized to announce a policy that sugar manufacturers need to include warning labels about sugar risks on their products, and is scheduled to regulate advertisements for foods including sugar exceeding a standard sugar content after 2010. Consequently, there is a need for the emergence of a new sweetener that may be substituted for sugar. In 1879, Ira Remsen from USA and Constantin Fahlberg from Germany discovered saccharin, which is 500 times sweeter than sugar. Saccharin has an advantage in that saccharin does not break down in the human body and is excreted from the human body, but has sparked a controversy that saccharin is a carcinogenic substance. Finally, although saccharin was proven to be harmless to the human body, saccharin is still scarcely used due to the disadvantage of the bitter aftertaste of saccharin. In 1937, the University of Illinois in USA found that sodium cyclohexylsulfamate has a sweet taste. With the trade name cyclamate, sodium cyclohexylsulfamate was first used in the beginning of 1950, and became popular on the global sweetener market in the 1960s. However, as sodium cyclohexylsulfamate was proven to be a carcinogenic substance, sodium cyclohexylsulfamate has been completely prohibited since the 1970s in Korea. An artificial sweetener most widely used in recent years is aspartame that was discovered in 1965 by James M. Schlatter. Aspartame has a sugar content about 180 to 200 times that of sugar. Aspartame is included in a majority of currently commercially available diet beverages, and thus produces phenylalanine during the metabolism process when aspartame is ingested into the human body. Consequently, aspartame has a disadvantage in that phenylketonuric patients who are congenitally deficient in a specific enzyme (phenylalanine hydroxylase) to break down phenylalanine cannot use aspartame.

There has been continuous research conducted to develop not only artificial sweeteners but also natural sweeteners, and as a result, a material referred to as stevioside was found to be present in the leaves of a perennial plant (*Stevia rebaudiana*) in the Asteraceae, which is classified as an herb. The natives living in the border between Paraguay and Brazil have used this material as a sweetener for over 400 years. In Korea, stevioside is sometimes added to a traditional distilled liquor called "soju" and is 200 times as sweet as sugar. Meanwhile, increasing attention has been recently paid to a sweetener protein extracted from a tropical fruit, and Thaumatin is a protein included in the fruit of a perennial plant (*Thaumatococcus daniellii*) referred to as a miracle fruit in Western Africa, and is 2,000 to 3,000 times as sweet as sugar. Monellin is a protein obtained from the fruit of a vine plant referred to as a serendipity berry growing in the rain forest area of Africa, and is 3,000 times as sweet as sugar. However, it is difficult to culture the serendipity berry and also to extract monellin from the fruit of the serendipity berry. Moreover, monellin has a disadvantage in that monellin has low thermal stability, and loses its 3-dimensional protein structure and thus does not show sweetness when being heat-treated in a food processing process. In order to overcome these disadvantages, there has been research conducted to enhance the thermal stability of the monellin using a protein engineering technique.

Meanwhile, brazzein is a sweetener protein firstly extracted from the fruit of *Pentadiplandra brazzeana* (Baillon) growing in West Africa [Ming et al., FEBS Letters, 355: 106-108, 1994]. Brazzein shows sweetness about 500 to 2,000 times or more that of sucrose [Jin et al., Chem. Senses. 28: 491-498, 2003], and is divided into two types: a major type and a minor type. The major type accounting for a majority of brazzein extracted from the plant has 54 amino acids including a pyroglutamic acid residue bound to an amino-terminal site. On the other hand, the minor type of brazzein has 53 amino acid residues without a pyroglutamic acid residue bound to an amino-terminal site, and shows stronger sweetness, about twice that of the major type of brazzein [Assadi-Porter et al., Arch., Biochem. Biophys. 376: 259-265, 2000]. Brazzein has a molecular weight of about 6.5 kDa, which is the smallest among the sweetener proteins, and is a monomer composed of one kind of subunit. Brazzein consists of a single polypeptide and is composed of one α-helix and two β-pleated sheets. Brazzein has very high thermal stability since brazzein has 8 cysteine residues to form 4 disulfide bonds in the molecule. In addition, brazzein shows very high solubility and pH stability in water [Gao et al., Int. J. Biol. Macromol. 24: 351-359, 1999].

U.S. Pat. No. 6,274,707 B1 and Assadi-Porter et al. (Assadi-Porter et al., Arch. Biochem. Biophys. [0006] 376: 259-265, 2000) describe a method of producing recombinant brazzein using a genetic engineering method by which the aforementioned brazzein is produced in *Escherichia coli*, and disclose the method including: synthesizing a gene encoding brazzein, inserting the gene into a recombinant vector containing a SNase gene to produce a new transformation vector, introducing the transformation vector into *E. coli*, and finally expressing and purifying a fusion protein linked with the SNase. However, since the brazzein fused and expressed with the SNase produces an insoluble inclusion body, and the insoluble inclusion body is refolded and separated and purified by a method of removing SNase and methionine (Met) using cyanobromide (CNBr), there is a disadvantage in that the method is technically complex and difficult so that it is very difficult to commercialize the recombinant brazzein by mass production. Accordingly, the present inventors have conducted prior research to solve the disadvantages of the existing researches, and registered a patent for a polynucleotide including an E. coli pelB signal sequence and a brazzein gene and a production method for brazzein using the same (Korean Patent No. 809100). Furthermore, in order to search for a natural sweetener having high thermal stability and showing excellent sweetness, the present inventors filed patent applications (Korean Patent Application Nos. 2007-0117013, 2008-0019008, and 2010-0016660, and International Patent Application No. PCT/KR2009/04855) for a production method for variants and multiple variants of amino acids at certain positions which are expected not to affect a structure in an amino acid constituting brazzein.

Throughout the present specification, a plurality of papers and patent documents are referenced, and citations thereof are indicated. The disclosure of each of the cited papers and patent documents is incorporated herein by reference in its entirety to describe the level of the technical field to which the present invention pertains and the content of the present invention more apparently.

SUMMARY OF THE INVENTION

The present inventors have made intensive studies to develop a new type of brazzein variant protein having increased sweetness compared to wild brazzein in the related art, and as a result, successfully prepared a multiple variant having amino acid variation at four different sites of wild brazzein and experimentally confirmed that the variant has far beyond increased sweetness compared to the wild brazzein and variants that have previously been developed, thereby completing the present invention.

Consequently, an object of the present invention is to provide a brazzein multiple variant having increased sweetness.

Another object of the present invention is to provide a nucleic acid molecule encoding the brazzein multiple variant.

Still another object of the present invention is to provide a recombinant vector including the nucleic acid molecule.

Yet another object of the present invention is to provide host cells that have been transformed with the recombinant vector.

Still yet another object of the present invention is to provide a method for producing the brazzein multiple variant.

Further another object of the present invention is to provide a food composition for increasing a sugar content, which includes the brazzein multiple variant as an active ingredient.

Still further another object of the present invention is to provide a use of the brazzein multiple variant for preparing a food composition for increasing a sugar content.

The objects and advantages of the present invention will be more apparent from the following detailed description, claims and drawings of the invention.

BRIEF DESCRIPTION OF THE DRAWINGS

FIG. 4a is a result of HPLC analysis of the brazzein multiple variant K4D_H30R_E35D_E40A, FIG. 4b is a result of HPLC analysis of the brazzein multiple variant K4E_H30R_E35D_E40A, FIG. 4c is a result of HPLC analysis of the brazzein multiple variant K4R_H30R_E35D_E40A, FIG. 4d is a result of HPLC analysis of the brazzein multiple variant K4D_H3ORE35D_E40K, FIG. 4e is a result of HPLC analysis of the brazzein multiple variant K4D_H30R_E35D_E40K, FIG. 4f is a result of HPLC analysis of the brazzein multiple variant K4R_H30R_E35D_E40K, FIG. 4g is a result of HPLC analysis of the brazzein multiple variant K4D_H30R_E35D_E40D, FIG. 4h is a result of HPLC analysis of the brazzein multiple variant K4E_H30R_E35D_E40D, FIG. 4i is a result of HPLC analysis of the brazzein multiple variant K4R_H30R_E35D_E40D, FIG. 4j is a result of HPLC analysis of the brazzein multiple variant K4D_H30R_E35D_E40R, FIG. 4k is a result of HPLC analysis of the brazzein multiple variant K4E_H30R_E35D_E40R, and FIG. 4l is a result of HPLC analysis of the brazzein multiple variant K4R_H30R_E35D_E40R.

DETAILED DESCRIPTION OF EXEMPLARY EMBODIMENTS

Figure 1:
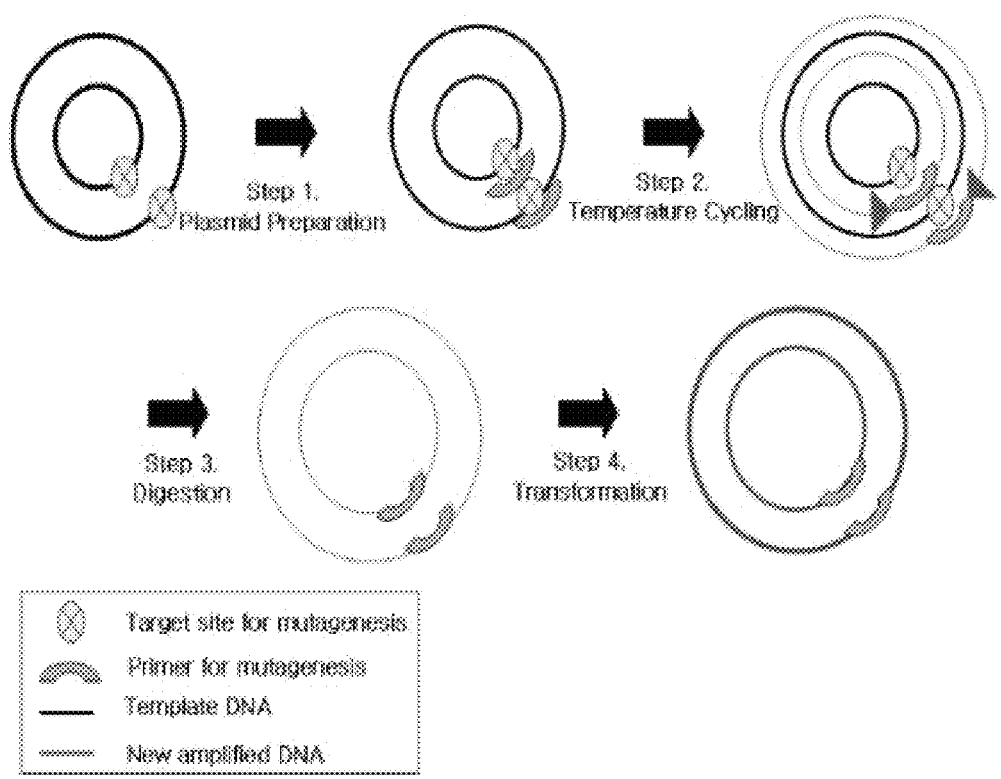
FIG. 1 is a view schematically illustrating a site-directed mutagenesis for preparing the brazzein multiple variant of the present invention in the following Example 1.

According to an aspect of the present invention, the present invention provides a brazzein multiple variant having any one amino acid sequence selected from the group consisting of SEQ ID NOS. 11 to 22.

The brazzein multiple variant of the present invention is a multiple variant in which a lysine residue, which is an amino acid at the fourth position, is substituted with each of aspartic acid, glutamic acid, or arginine in a tertiary brazzein variant having an amino acid sequence of SEQ ID NO. 1, 2, 3, or 4 H30R_E35D_E40K, H30R_E35D_E40A, H30R_E35D_E40D, or H30R_E35D_E40R.

As proven in a specific embodiment of the following present invention, the brazzein multiple variant protein of the present invention has increased sweetness about 2,500 to 3,500 times that of the wild brazzein.

According to another aspect of the present invention, the present invention provides a nucleic acid molecule encoding the brazzein multiple variant.

The term "nucleic acid molecule" used in the present specification has a meaning comprehensively including DNA (gDNA and cDNA) and RNA molecules, and a nucleotide, the basic building unit in the nucleic acid molecule, includes not only a natural nucleotide, but also an analogue in which a sugar or base site is modified (Scheit, Nucleotide Analogs, John Wiley, New York(1980); Uhlman and Peyman, Chemical Reviews, 90:543-584 (1990)).

According to preferred exemplary embodiments of the present invention, the nucleic acid molecule has any one nucleotide sequence selected from the group consisting of SEQ ID NOS. 23 to 34.

According to another aspect of the present invention, the present invention provides a recombinant vector including (i) a promoter and (ii) a nucleic acid molecule encoding the brazzein multiple variant operatively linked with the promoter.

According to preferred exemplary embodiments of the present invention, the nucleic acid molecule encoding the brazzein multiple variant in the recombinant vector may be linked with a nucleic acid molecule encoding an *E. coli* pelB signal sequence.

The *E. coli* pelB signal sequence is a kind of signal sequences for an *E. coli* cell membrane clearance (Rietsch et al., Proc. Natl. Acad. Sci. USA 93: 130408-13053, 1996, Raina et al., Ann. Rev. Microbiol. 51: 179-202, 1997, Sone et al., J. Biol. Chem. 272: 10349-10352, 1997), and when a brazzein multiple variant protein is synthesized, the signal sequence serves to induce an exact disulfide bond by transferring the protein to the *E. coli* cell membrane clearance, suppress the brazzein protein from forming an insoluble aggregate, and facilitate the purification process by minimizing unnecessary proteins derived from *E. coli*.

The pelB signal sequence is linked with the 5' end of the nucleic acid molecule encoding the brazzein multiple variant of the present invention so as to have the same frame during the translation into a protein, and preferably has a DNA nucleic acid base sequence of SEQ ID NO. 35.

The term "promoter" refers to a protein coding sequence or a DNA sequence which controls expression of a functional RNA.

The term "operatively linked" refers to a functional linkage between a nucleic acid expression control sequence (for example, a promoter sequence, a signal sequence, or array of transcription control factor binding positions) and another nucleic acid sequence, and the control sequence accordingly controls transcription and/or translation of the another nucleic acid sequence.

The vector in the present invention may be constructed through various methods publicly known in the art, and the specific method thereof is disclosed in Sambrook et al., Molecular Cloning, A Laboratory Manual, Cold Spring Harbor Laboratory Press (2001), which is incorporated by reference in the present specification. The recombinant vector of the present invention may be constructed as a vector for cloning or expression, and may be constructed using a prokaryotic cell or eukaryotic cell as a host. For example, when the vector of the present invention is an expression vector, and uses a prokaryotic cell as a host, it is common to include a strong promoter which may proceed transcription (for example, pLλ promoter, trp promoter, lac promoter, T7 promoter, tac promoter, and the like), a ribosomal binding site for translation initiation, and a transcription/translation termination sequence. When *Escherichia coli* (*E. coli*) is used as a host cell, the promoter and operator site of *E. coli* tryptophan biosynthesis pathway (Yanofsky, C., J. Bacteriol., 158:1018-1024 (1984)), and a leftward promoter of phage λ (pLλ, promoter, Herskowitz, I. and Hagen, D., Ann. Rev. Genet., 14: 399-445 (1980)) may be used as a regulatory site.

Meanwhile, when the vector of the present invention is an expression vector, and uses a eukaryotic cell as a host, it is possible to use a promoter derived from the genome of mammalian cells (for example: a metallothionein promoter), or a promoter derived from mammalian viruses (for example: an adenovirus late promoter, a vaccinia virus 7.5K promoter, a SV40 promoter, a cytomegalovirus promoter, and a tk promoter of HSV), and the vector of the present invention generally has a polyadenylation sequence as a transcription termination sequence.

The most preferred promoter in the vector of the present invention is an *E. coli* pelB promoter.

The vector of the present invention may include an antibiotic resistance gene typically used in the art as a selection marker, and examples thereof include ampicillin, gentamycin, carbenicillin, chloramphenicol, streptomycin, kanamycin, geneticin, neomycin, and a gene resistant to tetracycline, and the present invention is not limited thereto. The antibiotic resistance gene is operatively linked with a promoter for expressing the gene.

The vector which may be used in the present invention may be manufactured by manipulating a plasmid (for example: pSC101, ColE1, pBR322, pUC8/9, pHC79, pGEX series, pET series, pUC19, and the like), a phage (for example: λgt4•λB, λ-Charon, λΔz1, M13, and the like), or a virus (for example: SV40, and the like), which are frequently used in the art.

The vector of the present invention is preferably a vector for a prokaryotic cell, and includes a nucleic acid sequence which enables replication in a prokaryotic cell, particularly, *E. coli*. Consequently, the vector of the present invention includes an origin of replication of bacteria of colE1 or p15A, or an origin of replication of bacteriophage, such as f1 origin.

According to another aspect of the present invention, the present invention provides host cells that have been transformed with the recombinant vector.

A host cell, which is capable of stably and consecutively cloning or expressing the vector of the present invention, may be any host cell that is publicly known in the art, and examples of a prokaryotic cell include *E. coli* JM109, *E. coli* BL21, *E. coli* RR1, *E. coli* LE392, *E. coli* B, *E. coli* X 1776, *E. coli* W3110, strains of *Bacillus* species such as *Bacillus* subtilis or *Bacillus thuringiensis*, intestinal bacteria and strains such as *Salmonella typhymurium, Serratia marcescens*, and various *Pseudomonas* species, and the like.

When the vector of the present invention is transformed in a eukaryotic cell, it is possible to use yeast (*Saccharomyce cerevisiae*), an insect cell, a human cell (for example, Chinese hamster ovary (CHO) cell line, W138, BHK, COS-7, 293, HepG2, 3T3 , RN, and MDCK cell lines), a plant cell, and the like as a host cell.

A method of delivering the vector of the present invention to host cells may be performed by using a $CaCl_2$ method (Cohen, S. N. et al., Proc. Natl. Acac. Sci., USA, 9:2110-2114 (1973)), a Hanahan method (Cohen, S N et al., Proc. Natl. Acac. Sci. USA, 9:2110-2114 (1973); and Hanahan, D., J. Mol. Biol., 166:557-580 (1983)), an electroporation method (Dower, W. J. et al., Nucleic. Acids Res., 16:6127-6145 (1988)), and the like, when the host cells are a prokaryotic cell. Further, when the host cells are eukaryotic cells, the vector may be injected into the host cells by a microinjection method (Capecchi, M. R., Cell, 22:479 (1980)), a calcium phosphate precipitation method (Graham, F. L. et al., Virology, 52: 456 (1973)), an electroporation method (Neumann, E. et al., EMBO J., 1:841 (1982)), a liposome-mediated transformation method (Wong, T. K. et al., Gene, 10:87 (1980)), a DEAE-dextran treatment method (Gopal, Mol. Cell Biol., 5: 1188-1190 (1985)), and gene bombardment (Yang et al., Proc. Natl. Acad. Sci., 87: 9568-9572 (1990)) and the like.

According to still another aspect of the present invention, the present invention provides a method for making a brazzein multiple variant, including the following steps: (a) culturing host cells that have been transformed with a recombinant vector which expresses the above-described brazzein multiple variant; and (b) separating a brazzein multiple variant protein from the cultured host cells.

The host cells that have been transformed with a vector which expresses the brazzein multiple variant of the present invention are cultured under suitable culture conditions using an appropriate medium which may induce expression of the brazzein multiple variant. The medium and culture conditions for culturing the host cells are publicly known to a person skilled in the art, and the person skilled in the art may modify the publicly known medium and culture conditions suitably for the present invention and use the modified medium and culture conditions.

According to preferred exemplary embodiments of the present invention, the host cells which express the brazzein multiple variant of the present invention are *Escherichia coli* (*E. coli*).

While *E. coli* is cultured as the host cells, the brazzein multiple variant is expressed by a nucleic acid expression control sequence in the expression vector.

According to preferred exemplary embodiments of the present invention, the brazzein multiple variant of the present invention includes a pelB signal sequence, a brazzein multiple variant protein is transferred to the *E. coli* cell membrane clearance by the pelB signal sequence, and the pelB signal sequence is removed by an *E. coli* signal peptidase.

A brazzein multiple variant expressed in *E. coli* is included in the *E. coli* cell membrane clearance, and thus may be separated by using a publicly known method of separating a protein from the *E. coli* cell membrane clearance (Snyder et al., J. Bacteriology 177: 953963, 1995). For example, the separation may be performed by a method including: collecting the cultured *E. coli*, suspending the cultured *E. coli* in a 30 mM Tris-hydrochloric acid (Tri-HCl, pH 8) solution including 20% sucrose, and eluting a protein of the *E. coli* cell membrane clearance using an EDTA (pH 8) solution and $MgSO_4$.

The method for separating the brazzein multiple variant of the present invention from the *E. coli* cell membrane clearance proteinmay be performed by various separation and purification methods publicly known in the art, and for example, it is possible to use a technique such as salting-out (ammonium sulfate precipitation and sodium phosphate precipitation), solvent precipitation (a protein fractionation precipitation using acetone, ethanol, and the like), dialysis, gel filtration, ion exchange chromatography, reverse phase chromatography, and affinity ultrafiltration, alone or in combination.

Since the brazzein protein is stable to heat, separation of the brazzein multiple variant of the present invention may be performed by heat treatment, and for example, other proteins except for brazzein is thermally denatured by heating the *E. coli* cell membrane clearance at 70 to 90° C. for 15 to 60 minutes, and then only the brazzein variant protein may be separated from the thermally denatured proteins through centrifugation at 18,000 g at 4° C. for 30 minutes.

Characteristics of the brazzein multiple variant protein of the present invention are summarized as follows.

(i) Molecular weight: 6304 to 6389 Da
(ii) High thermal stability and acid resistance
(iii) High water solubility
(iv) Degree of increased sweetness compared to sucrose: 1,250,000 to 2,800,000 times
(v) Degree of increased sweetness compared to the wild brazzein minor type: 1,500 to 3,570 times That is, the brazzein multiple variant of the present invention is enhanced 1,500 to 3,570 times as sweet as the wild brazzein minor type protein.

The degree of increased sweetness as described above is a value far beyond increased even when compared to those of the brazzein variants which the present inventors have previously developed (Korean Patent Application Nos. 2007-0117013, 2008-0019008, and 2010-0016660).

According to yet another aspect of the present invention, the present invention provides a food composition for increasing a sugar content, which includes the brazzein multiple variant as an active ingredient.

The food composition of the present invention includes all the forms such as functional food, nutritional supplement, health food, and food additives. The type of food composition may be prepared into various forms according to a typical method publicly known in the art. Examples of the forms include beverages (including an alcoholic beverages), fruit and processed food thereof (for example: canned fruit, bottled food, jam, marmalade, and the like), fish, meat and processed food thereof (for example: ham, sausage and corned beef, and the like), bread and noodles (for example: thick wheat noodles, buckwheat noodles, instant noodles, spaghetti, macaroni, and the like), fruit juice, various drinks, cookies, wheat-gluten, dairy products (for example: butter, cheese, and the like), edible vegetable oils, margarine, vegetable protein, retort foods, frozen food and various seasonings (for example: soybean paste, soy sauce, sauce, and the like).

In order to use a food composition containing the brazzein multiple variant of the present invention as a form of food additive, the food composition may be prepared in a form of powder or concentrate, and used.

The brazzein multiple variant of the present invention in the food composition of the present invention may be included in a content range of 0.01 to 10 wt % based on the total weight of the composition.

According to still yet another aspect of the present invention, the present invention provides a use of the brazzein multiple variant for preparing a food composition for increasing a sugar content.

[Advantageous Effects]

The present invention relates to: a novel brazzein multiple variant having increased sweetness; a nucleic acid molecule encoding the variant; a recombinant vector including the nucleic acid molecule; host cells that have been transformed with the recombinant vector; a method for making the variant; and a food composition for increasing a sugar content, which includes the variant as an active ingredient. The brazzein multiple variant of the present invention is at least about two million times or more as sweet as sucrose (sugar) in the same amount, and the sweetness is far beyond increased even compared to the sweetness of wild-type brazzein and brazzein variants that have previously been developed. Consequently, the brazzein variant of the present invention can be used in a very small amount to bring out the desired sweetness, and can be used to replace sugar or other sweeteners in food.

[Best Mode]

Hereinafter, the present invention will be described in more detail through the Examples. These Examples are provided only for more specifically describing the present invention, and it will be obvious to a person with ordinary skill in the art to which the present invention pertains that the scope of the present invention is not limited by these Examples according to the gist of the present invention.

EXAMPLES

Example 1

Preparation of Brazzein Multiple Variant

1. Design of Primer

A site-directed mutagenesis was used to design an oligonucleotide primer such that the lysine (K) residue, which is the 4th amino acid in the amino acid sequence of a tertiary brazzein variant (based on the minor type), was mutated each with aspartic acid, glutamic acid, and arginine, and Cosmo Genetech Co., Ltd., (Seoul, Korea) was requested to synthesize the designed primer (Table 1). In order to enhance the efficiency of bases to be converted in the variant, the oligonucleotide primer to be synthesized was designed so as to have a length of 30 mer or less. The base sequence of brazzein was listed on both sides of a base to be converted, and two oligonucleotide primers designed to make one variant were allowed to be complementary to each single strand of brazzein.

TABLE 1

| Template | Variant | Site-directed mutagenesis primer base sequence |
|---|---|---|
| pET-26b(+)-Brazzein (H30R_E35D_E40K) | K4D | 5'-GAC AAA TGC GAT AAA GTT TAC GAA AAT TAC-3' (Forward primer; SEQ ID NO. 5) |
| | | 5'-GTA ATT TTC GTA AAC TTT ATC GCA TTT GTC-3' (Reverse primer; SEQ ID NO. 6) |
| | K4E | 5'-GAC AAA TGC GAA AAA GTT TAC GAA AAT TAC-3' (Forward primer; SEQ ID NO. 7) |
| | | 5'-GTA ATT TTC GTA AAC TTT TTC GCA TTT GTC-3' (Reverse primer; SEQ ID NO. 8) |
| | K4R | 5'-GAC AAA TGC CGC AAA GTT TAC GAA-3' (Forward primer; SEQ ID NO. 9) |
| | | 5'-TTC GTA AAC TTT GCG GCA TTT GTC-3' (Reverse primer; SEQ ID NO. 10) |

2. Manufacture of Variant

In order to manufacture a variant, a primer including a DNA sequence of an amino acid to be substituted was synthesized, and then the variant was prepared by using a QuickChange™ Site-Directed Mutagenesis Kit from Stratagene Corporation. In manufacturing the brazzein variant, pET-26b(+)-Brazzein(H30R_E35D_E40K), pET-26b(+)-Brazzein(H30R_E35D_E40R), pET-26b(+)-Brazzein(H30R_E35D_E40D), and pET-26b(+)-Brazzein(H30R_E35D_E40R) vectors, which are simple in expression and purification processes, were used as templates. The template vector is a vector including a nucleic acid molecule encoding proteins of tertiary brazzein variants H30R_E35D_E40K (SEQ ID NO. 1), H30R_E35D_E40A (SEQ ID NO. 2), H30R_E35D_E40D (SEQ ID NO. 3), and H30R_E35D_E40R (SEQ ID NO. 4), with 30th amino acid, 35th amino acid, and 40th amino acid mutated based on the brazzein minor-type amino acid sequence.

First, a reaction solution including 10 ng of a template DNA nucleic acid molecule, a dNTP mixture at each final concentration of 0.2 mM, a synthetic primer including 125 ng of a mutated base, 5 µl of a 10× reaction buffer, and 1 µl of a PfuTurbo DNA polymerization enzyme (2.5 U/µl) was prepared in a total volume of 50 µl, and then a polymerase chain reaction (PCR) was performed. The PCR reaction conditions were as follows: denaturation at 95° C. for 30 seconds, followed by annealing at 55° C. for 1 minute. And then, the synthesis of the gene by means of the polymerase was performed at 68° C. for 15 minutes. The condition was defined as one cycle, and this cycle was repeated 16 times to perform a reaction. After the reaction was completed, a product amplified was confirmed by electrophoresis in a 1.0% agarose gel. The confirmed product was treated with a Dpn I restriction enzyme at 37° C. for 1 hour, and then transformed with an E. coli DH5α (see FIG. 1). The transformed DH5α was cultured in an LB-agar plate containing 30 µg/ml of kanamycin for 12 hours to select a transformant. The selected colony was cultured to separate DNA therefrom. The genes confirmed to be variants through a base sequencing analysis were transformed with an E. coli BL21 star (DE3), and then used in mass expression. All three variants were successfully prepared, and purified by using the same method as in a recombinant brazzein expressed in a pET-26b(+)-brazzein (Met-) gene.

Based on the tertiary brazzein variants H30R_E35D_E40K H30R_E35D_E40A, H30R_E35D_E40R, and H30R_E35D_E40R, variants in which 4th lysine amino acid prepared by the method was substituted for aspartic acid, glutamic acid, or arginine are summarized and shown in the following Table 2.

TABLE 2

| Template | Muta-genesis Position | Amino acid residue mutagenesis and residue characteristics | | Name of variant |
|---|---|---|---|---|
| | | Before mutagenesis | After mutagenesis | |
| pET-26b(+)-Brazzein (H30R_E35D_E40K) | 4th | Lys(K), Positive | Asp(D), Negative | K4D_H30R_E35D_E40K (SEQ ID NO. 11) |
| | 4th | Lys(K), Positive | Glu(E), Negative | K4E_H30R_E35D_E40K (SEQ ID NO. 12) |
| | 4th | Lys(K), Positive | Arg(R), Negative | K4R_H30R_E35D_E40K (SEQ ID NO. 13) |
| pET-26b(+)-Brazzein (H30R_E35D_E40A) | 4th | Lys(K), Positive | Asp(D), Negative | K4D_H30R_E35D_E40A (SEQ ID NO. 14) |
| | 4th | Lys(K), Positive | Glu(E), Negative | K4E_H30R_E35D_E40A (SEQ ID NO. 15) |
| | 4th | Lys(K), Positive | Arg(R), Negative | K4R_H30R_E35D_E40A (SEQ ID NO. 16) |
| pET-26b(+)-Brazzein (H30R_E35D_E40D) | 4th | Lys(K), Positive | Asp(D), Negative | K4D_H30R_E35D_E40D (SEQ ID NO. 17) |
| | 4th | Lys(K), Positive | Glu(E), Negative | K4E_H30R_E35D_E40D (SEQ ID NO. 18) |
| | 4th | Lys(K), Positive | Arg(R), Negative | K4R_H30R_E35D_E40D (SEQ ID NO. 19) |
| pET-26b(+)-Brazzein (H30R_E35D_E40R) | 4th | Lys(K), Positive | Asp(D), Negative | K4D_H30R_E35D_E40R (SEQ ID NO. 20) |
| | 4th | Lys(K), Positive | Glu(E), Negative | K4E_H30R_E35D_E40R (SEQ ID NO. 21) |
| | 4th | Lys(K), Positive | Arg(R), Negative | K4R_H30R_E35D_E40R (SEQ ID NO. 22) |

3. DNA Base Sequencing Analysis

The variant vector pET-Brazzein including a brazzein multiple variant gene which included a mutated base sequence obtained by the PCR was purified from the transformed *E. coli* DH5α to confirm a gene base sequence. Cosmo Genetech Co., Ltd., was requested to analyze the gene base sequence.

Example 2

Expression and Purification of Brazzein Multiple Variant

1. Mass Expression of Variant

For the long-time storage of the pET-Brazzein variant/BL21 star (DE3) manufactured in Example 1, a liquid culture sample was prepared into a 20% glycerol stock state and freeze-stored at −70° C. For mass expression of the pET-Brazzein variant/BL21 star (DE3), the sample was cultured in a 1 L LB medium including 30 μg/ml of kanamycin for 8 hours or more without addition of an expression inducer isopropyl-β-D-thiogalactopyranoside (IPTG) to induce mass expression. From the mass-expressed culture solution, bacteria were collected at 4° C. and 8,000 g for 10 minutes by using a refrigerated centrifuge, and then freeze-stored at −20° C. until being used for purification.

2. Purification of Variant Protein

A 20 mM tris-HCl buffer (pH 8.0) was used to sufficiently disentangle the freeze-stored bacteria cells such that aggregates were not produced, and then an ultrasonic homogenizer was used to destroy cell membranes under conditions of 4° C., 30 to 40 watts, and an amplitude of 8%, which are common *E. coli* fragmentation conditions, for 15 minutes. After cells were fragmented, the fragmented cells were centrifuged at 4° C. and 30,000 g for 20 minutes to separate proteins and other cell impurities. For purification of the brazzein variant protein, a method described in the previous research methods was used (Lee et al., 2010). In the protein expression process, an inclusion body was produced to obtain most of the insoluble fractions. The obtained insoluble fraction was solubilized with a solubilization buffer, and then refolded for 24 hours to obtain a solubilized brazzein having activity. The solubilized brazzein was dialyzed in tertiary distilled water for 24 hours. Finally, the solubilized brazzein was heated at 85° C. for 30 minutes, and subjected to centrifugation to obtain pure brazzein. About 6 mg of purified brazzein per 1 L of the culture solution could be obtained, and was quantified through BCA assay.

3. Quantity of Variant Protein

The quantity of the brazzein variant protein was measured by the BCA assay (Pierce Chemical Co., Rockford, Ill., USA) method, and bovine serum albumin (BSA) and wild-type brazzein were used as standard proteins at 562 nm to prepare a standard curve, and then the standard curve was used to measure the concentration of the protein. A protein quantification assay purchased from Bio-Rad Corporation and the purified brazzein variant were reacted at 60° C. for 30 minutes, and then absorbance was measured at 562 nm to determine the concentration of the protein.

4. Electrophoresis Analysis of Variant Protein

Figure 2:
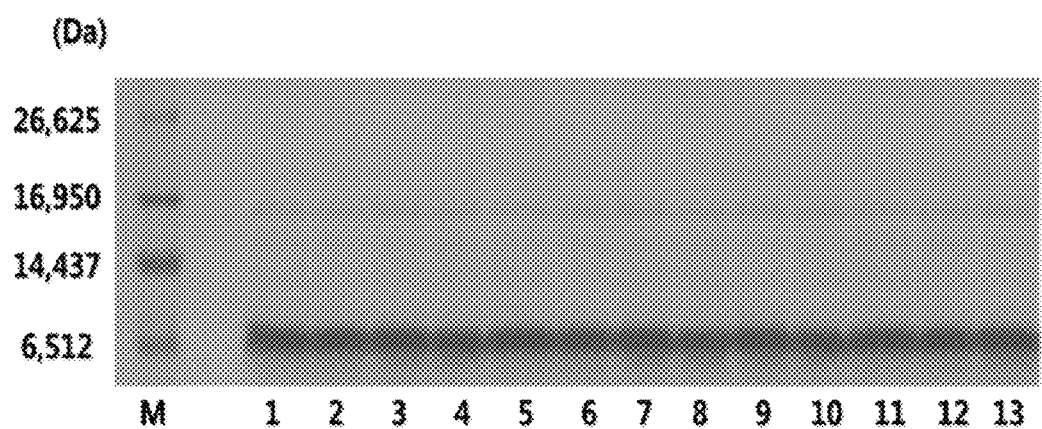
FIG. 2 is a result obtained by subjecting the brazzein multiple variant of the present invention purified in Escherichia coli (E. coli) without heat treatment to SDS-PAGE analysis (16.5% Tris-tricine gel). Lane M: SDS-PAGE polypeptide molecular weight marker; Lane 1: Wild-type brazzein (minor type); Lane 2: Brazzein multiple variant K4D_H30R_E35D_E40A; Lane 3: Brazzein multiple variant K4E_H30R_E35D_E40A; Lane 4: Brazzein multiple variant K4R_H30R_E35D_E40A; Lane 5: Brazzein multiple variant K4D_H30R_E35D_E40K; Lane 6: Brazzein multiple variant K4E_H30R_E35D_E40K; Lane 7: Brazzein multiple variant K4R_H30R_E35D_E40K; Lane 8: Brazzein multiple variant K4D_H30R_E35D_E40D; Lane 9: Brazzein multiple variant K4E_H30R_E35D_E40D; Lane 10: Brazzein multiple variant K4R_H30R_E35D_E40D; Lane 11: Brazzein multiple variant K4D_H30R_E35D_E40R; Lane 12: Brazzein multiple variant K4E_H30R_E35D_E40R; Lane 13: Brazzein multiple variant K4R_H30R_E35D_E40R.
Figure 3:
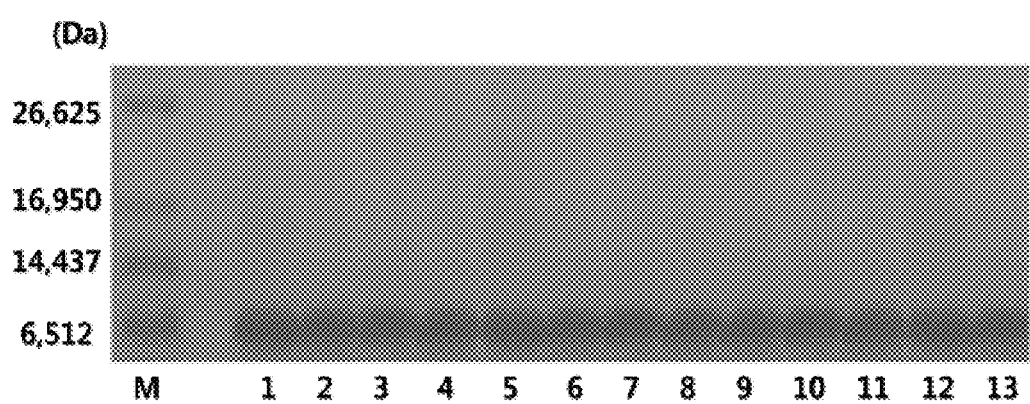
FIG. 3 is a result obtained by subjecting the brazzein multiple variant of the present invention purified by performing heat treatment to SDS-PAGE analysis (16.5% Tris-tricine gel). Lane M: SDS-PAGE polypeptide molecular weight marker; Lane 1: Wild-type brazzein (minor type); Lane 2: Brazzein multiple variant K4D_H30R_E35D_E40A; Lane 3: Brazzein multiple variant K4E_H30R_E35D_E40A; Lane 4: Brazzein multiple variant K4R_H30R_E35D_E40A; Lane 5: Brazzein multiple variant K4D_H30R_E35D_E40K; Lane 6: Brazzein multiple variant K4E_H30R_E35D_E40K; Lane 7: Brazzein multiple variant K4R_H30R_E35D_E40K; Lane 8: Brazzein multiple variant K4D_H30R_E35D_E40D; Lane 9: Brazzein multiple variant K4E_H30R_E35D_E40D; Lane 10: Brazzein multiple variant K4R_H30R_E35D_E40D; Lane 11: Brazzein multiple variant K4D_H30R_E35D_E40R; Lane 12: Brazzein multiple variant K4E_H30R_E35D_E40R; Lane 13: Brazzein multiple variant K4R_H30R_E35D_E40R.
Figure 4A:
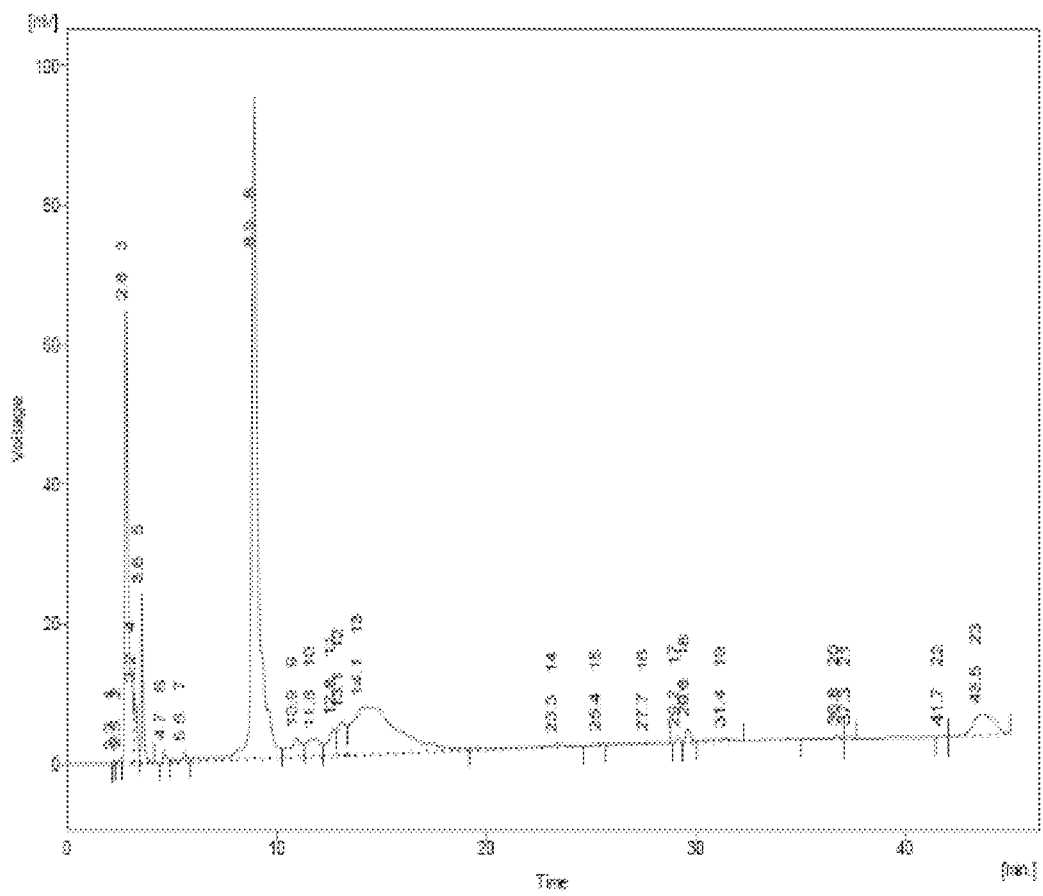
FIGS. 4a to 4l illustrate the results of HPLC analysis of the brazzein multiple variants of the present invention. The peaks illustrated at about 9 minute positions indicate the brazzein protein, and the peaks at 2.5 to 3.5 minute positions indicate a buffer.
Figure 4B:
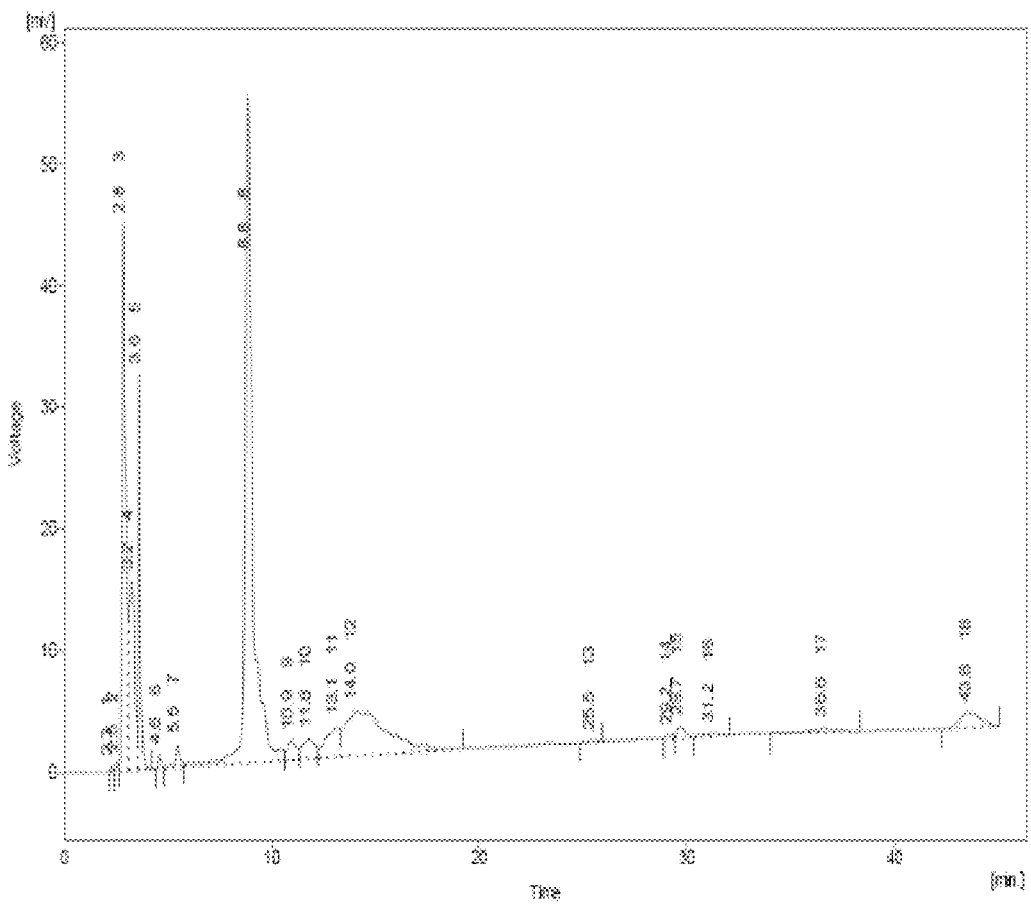
Figure 4C:
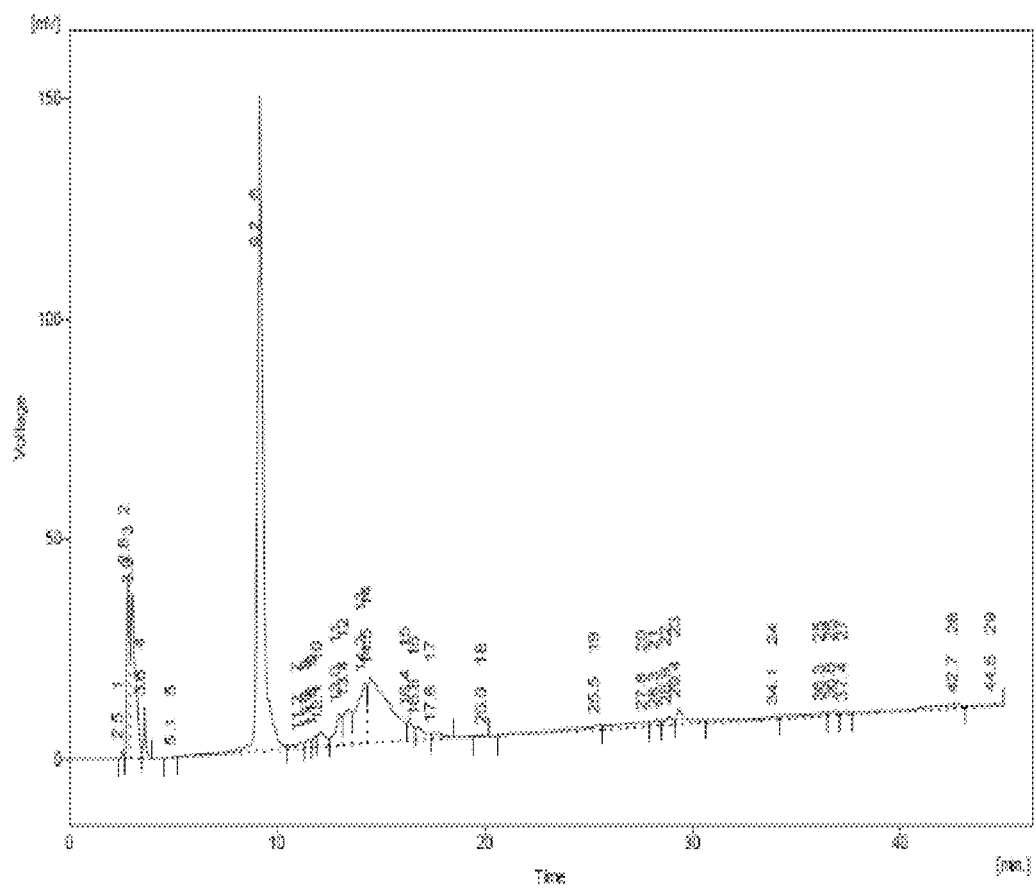
Figure 4D:
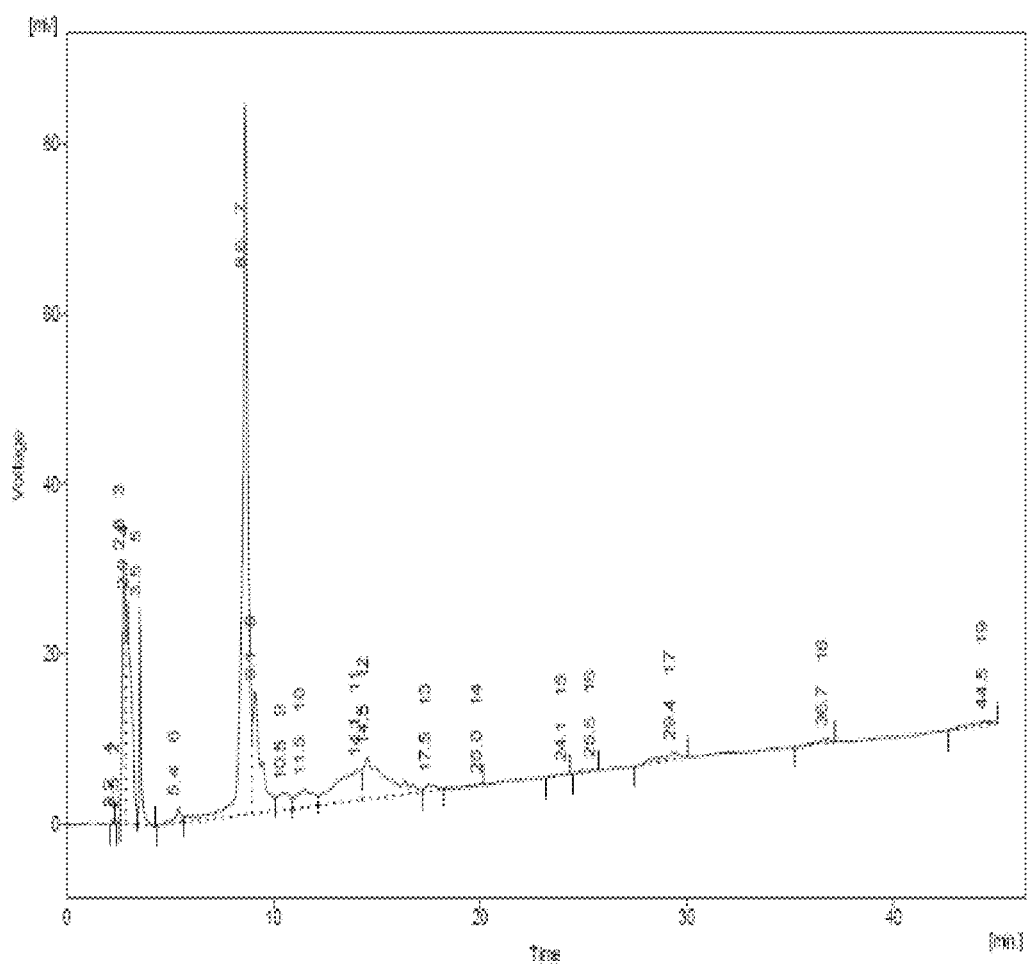
Figure 4E:
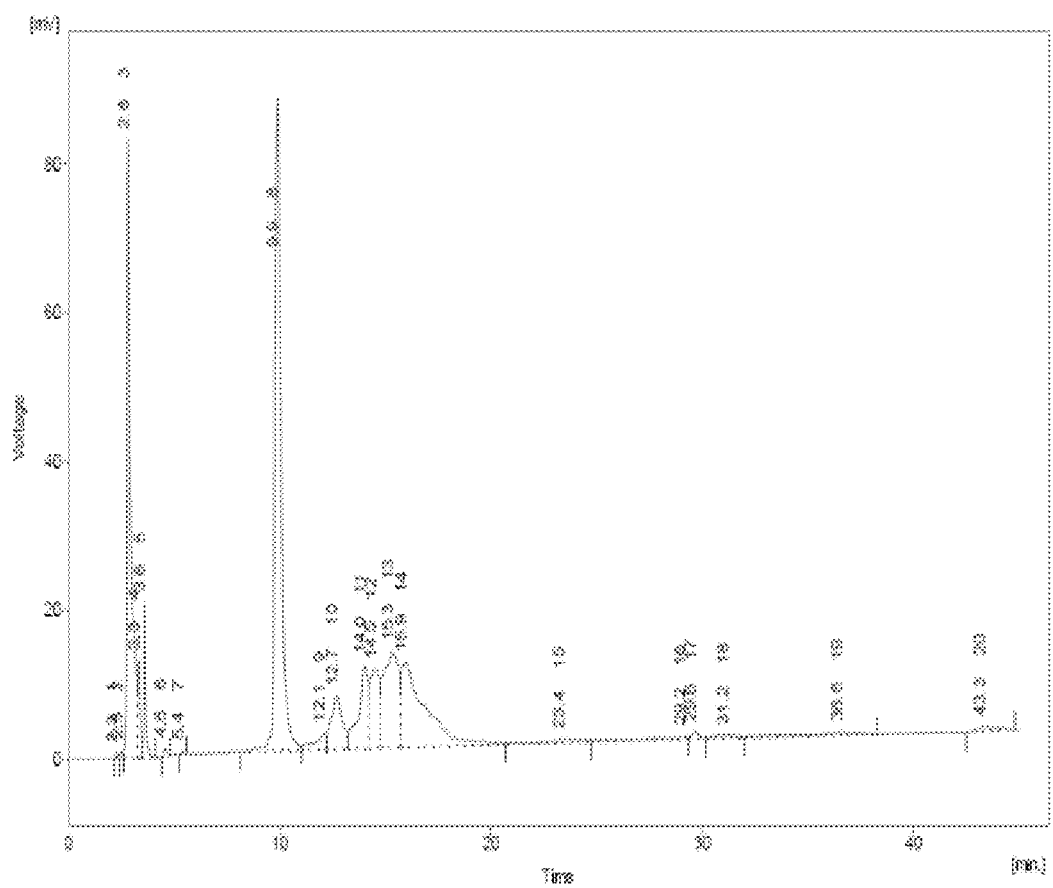
Figure 4F:
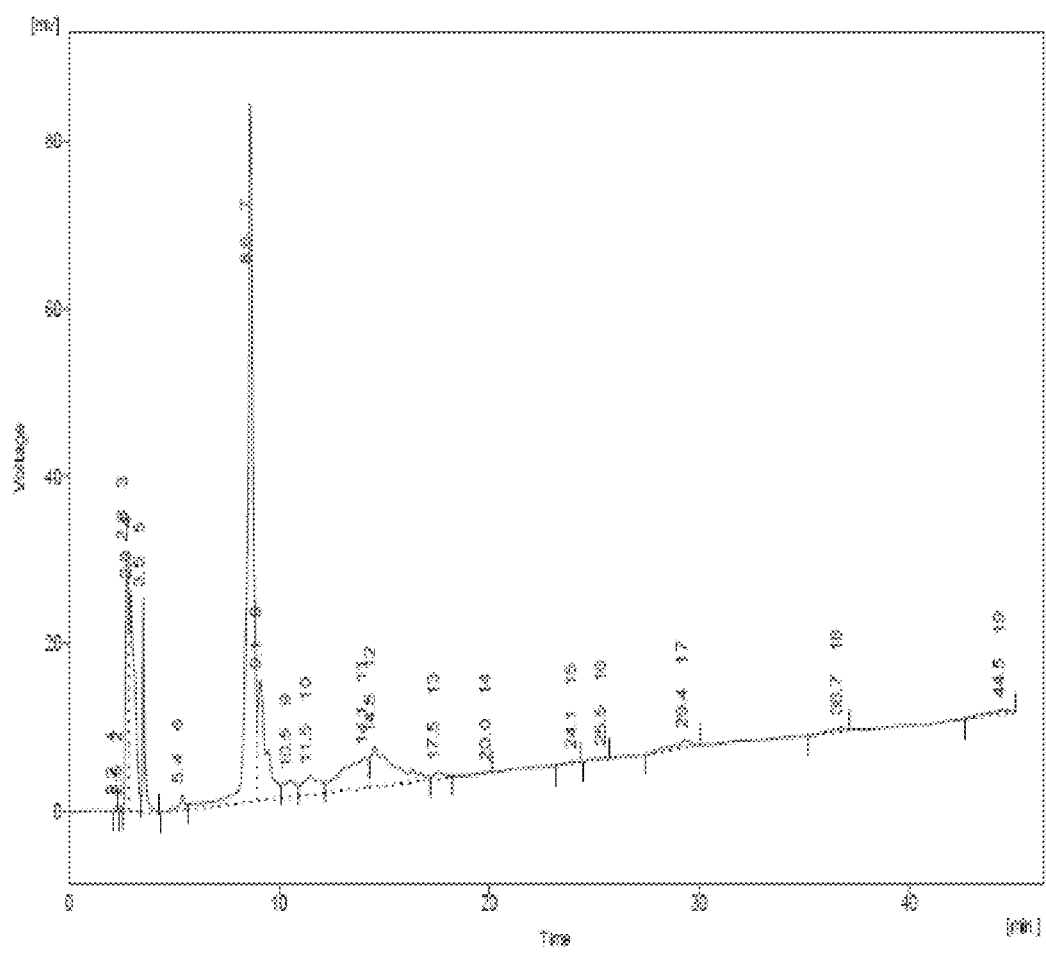
Figure 4G:
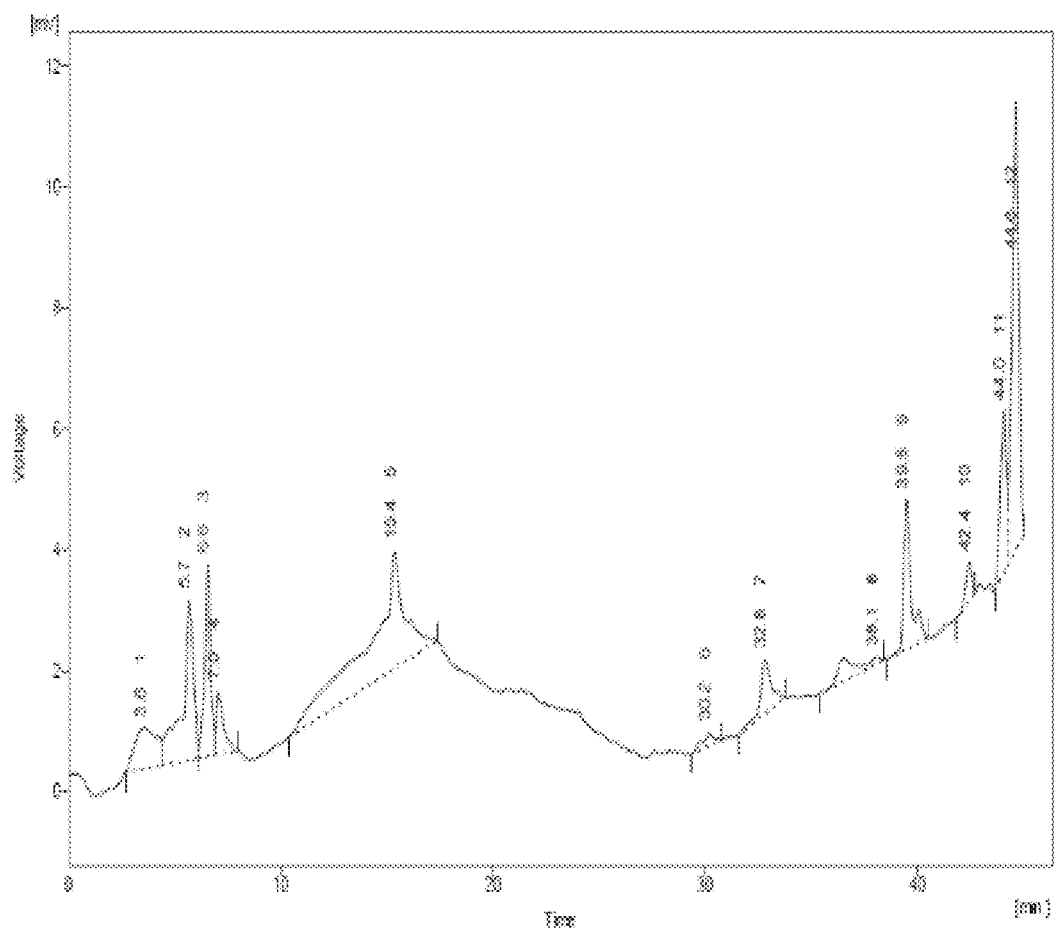
Figure 4H:
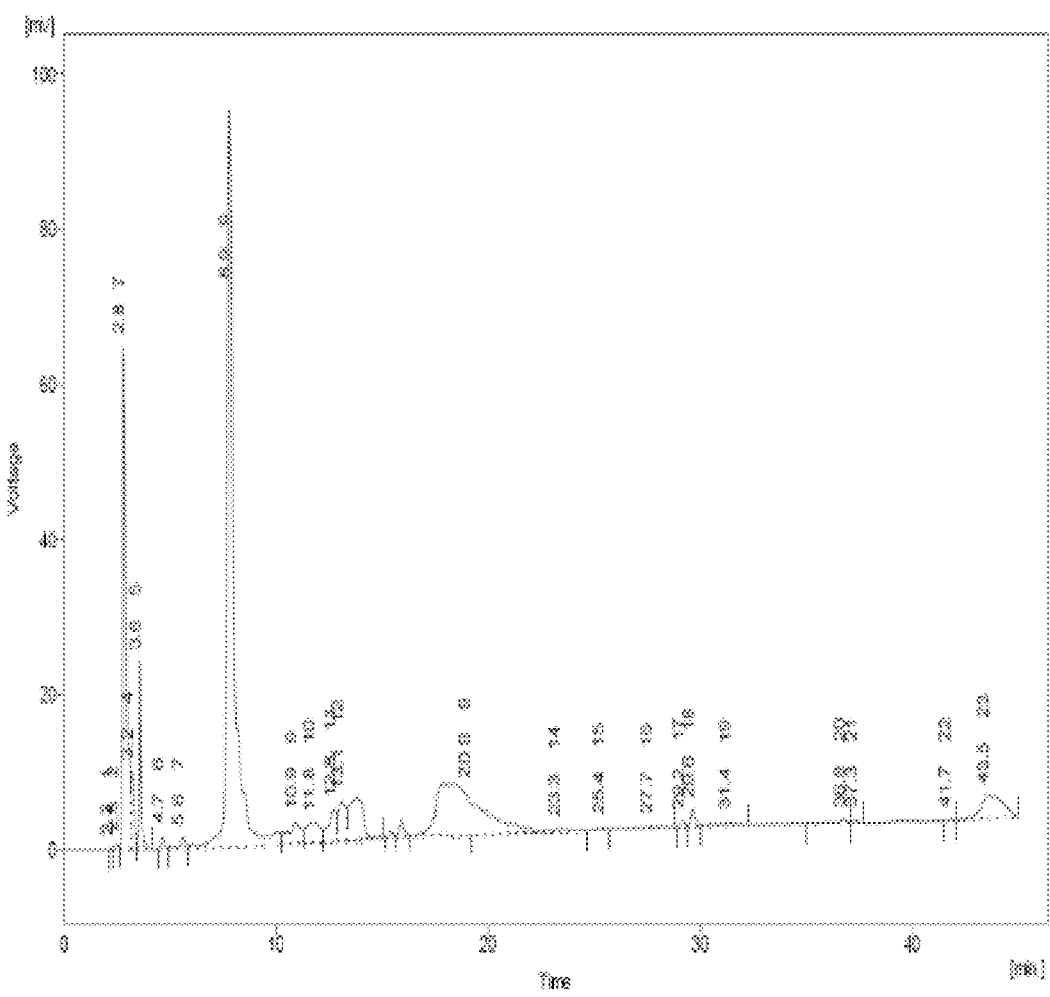
Figure 4I:
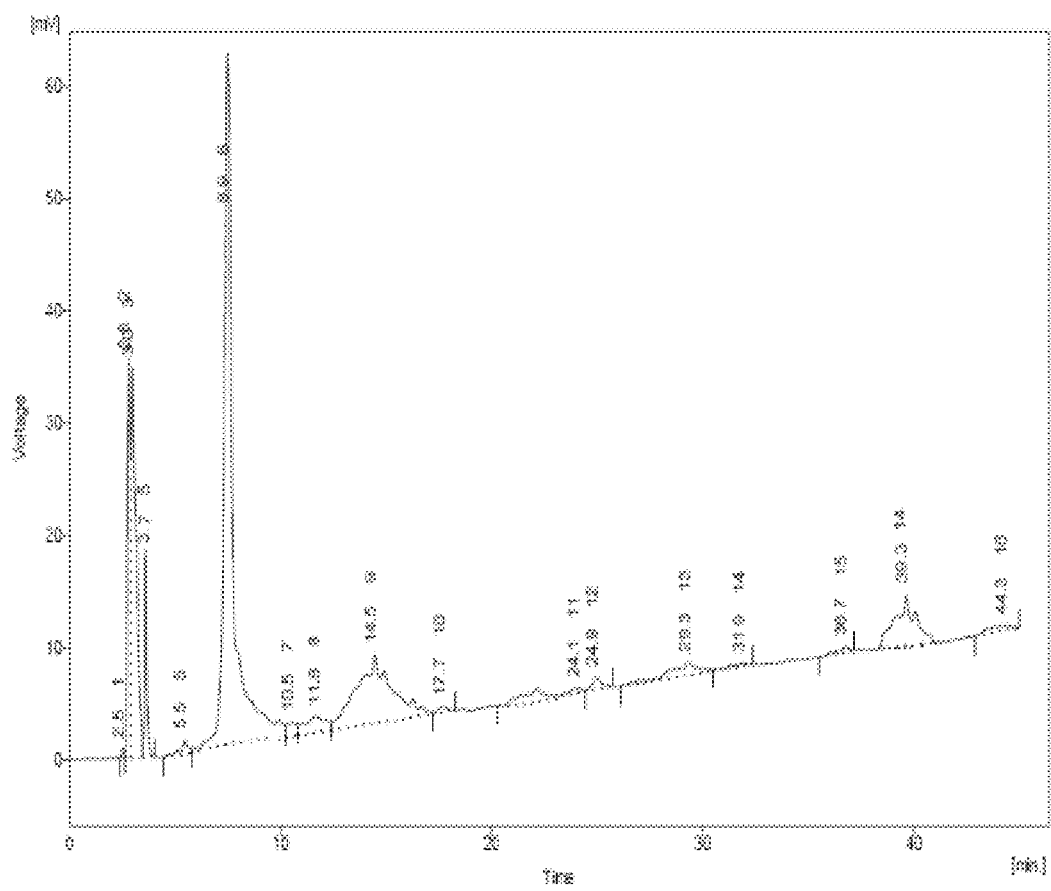
Figure 4J:
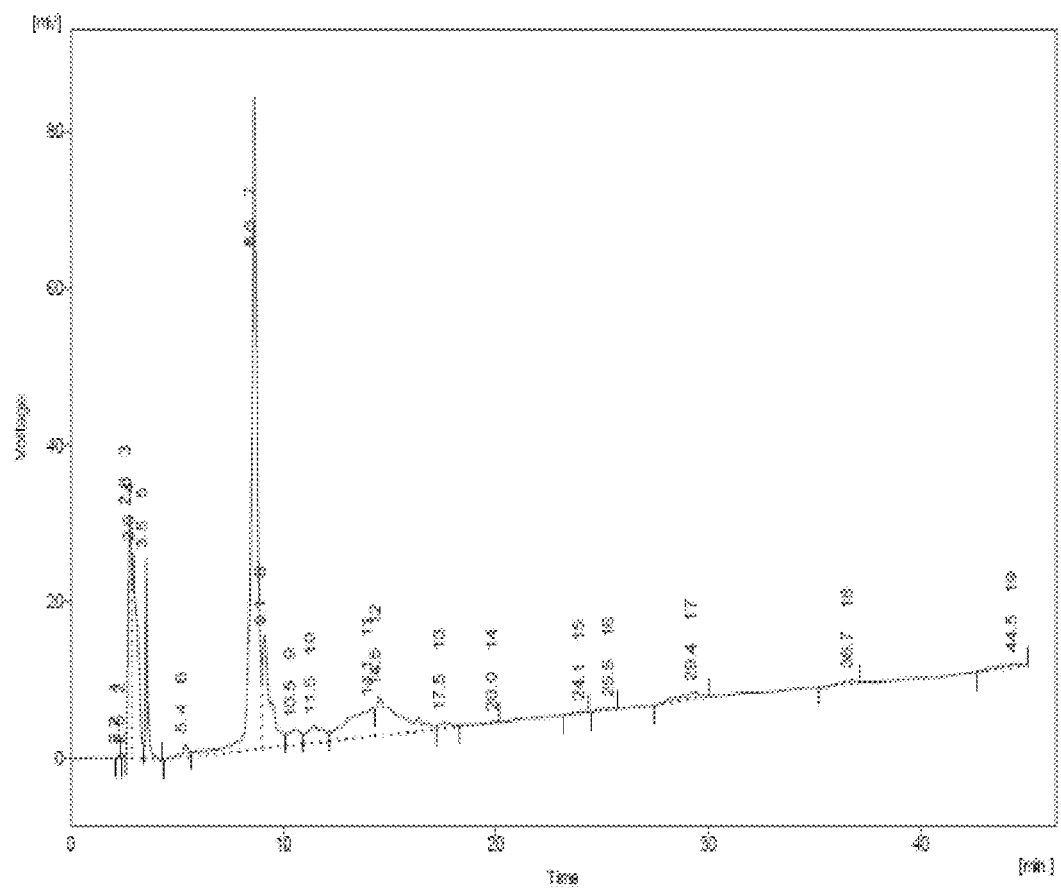
Figure 4K:
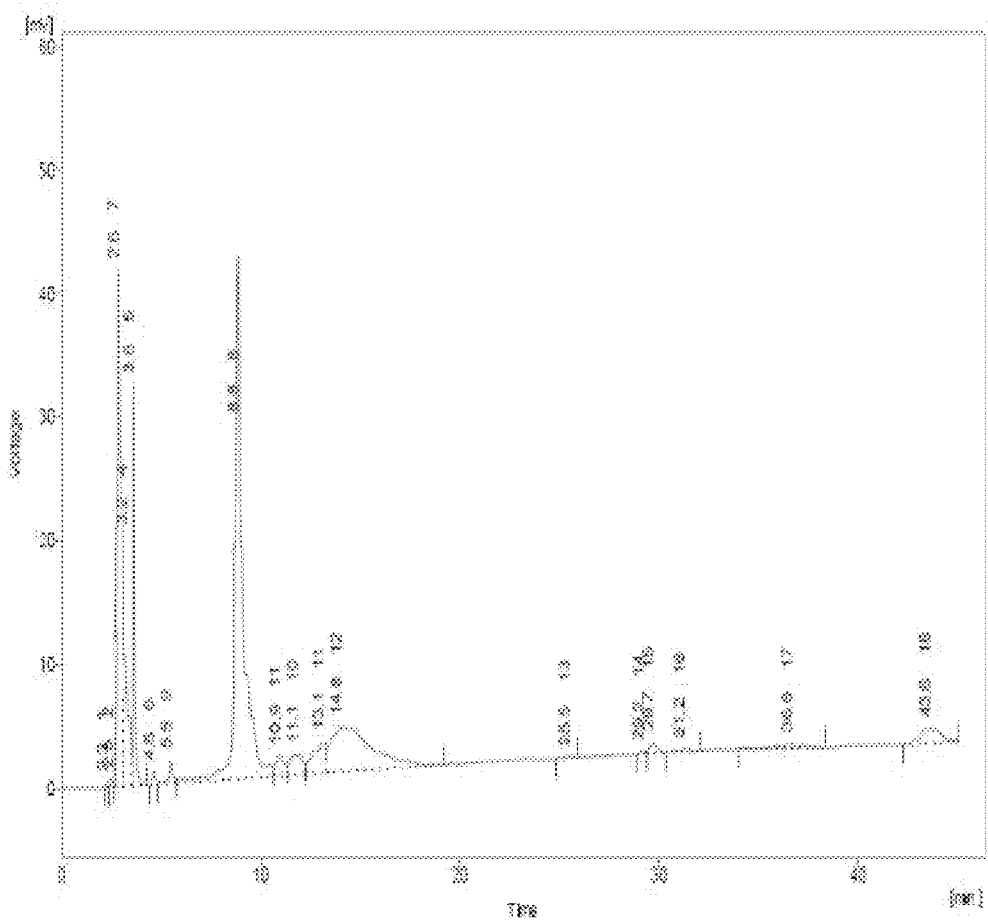
Figure 4L:
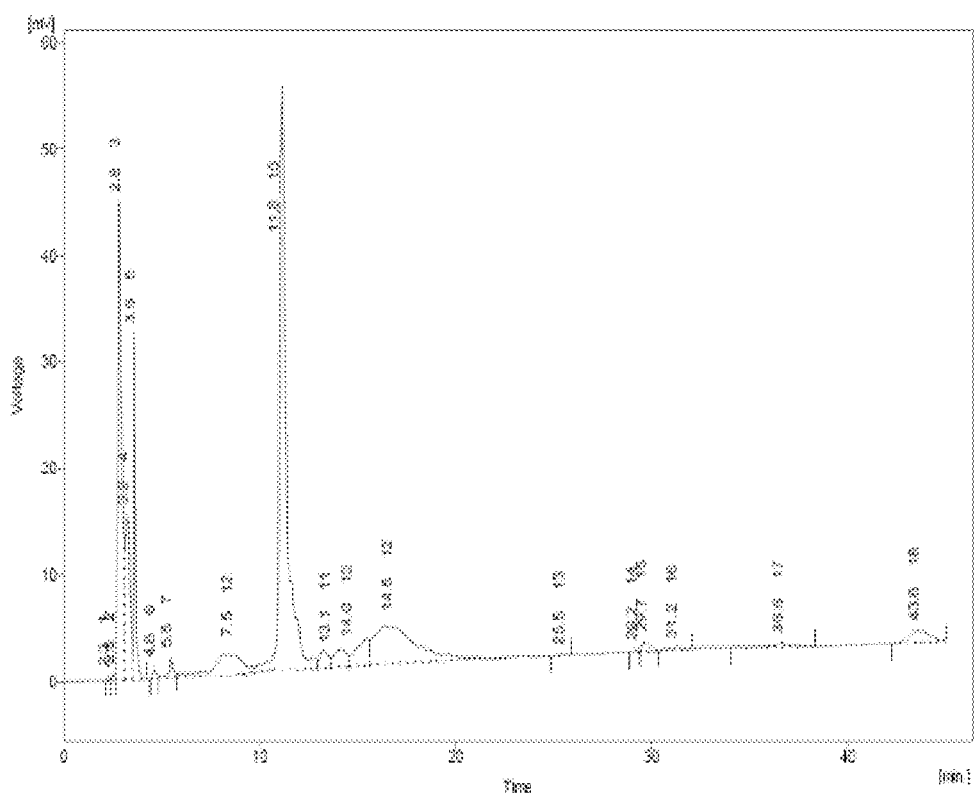

In order to measure the purity of the protein, SDS-PAGE analysis was performed. For the Tris-tricine gel, a 16.5% gel was prepared according to the Schagger and von Jagow (1987) method, and used. The gel subjected to electrophoresis was stained with coomassie brilliant blue R-250, and was sufficiently discolored to confirm the purity of the protein. In this case, as the used molecular weight standard proteins, polypeptide SDS-PAGE molecular weight standards from Bio-Rad Corporation, which included Triose-phosphate isomerase (26.6 kDa), Myoglobin (17 kDa), α-Lactalbumin (14.4 kDa), and Aprotinin (6.5 kDa), were used. As a result of SDS-PAGE, a pure brazzein variant protein band having about 6.5 kD was confirmed (see FIGS. 2 and 3).

5. High-Performance Liquid Chromatography (HPLC) Analysis

HPLC analysis was performed in order to confirm whether the purified brazzein variant was an active-type. A 305 system manufactured by Gilson, Inc., was used as the HPLC device, a C18 5 micron 150×4.6 column was used as a column for HPLC analysis, and analysis was performed under the concentration gradient conditions using a detection wavelength of 210 nm, a column temperature of normal temperature, a flow rate of 0.5 ml/min, and a mobile phase solvent composed of 0.05% TFA-distilled water as A solvent and 0.05% TFA-acetonitrile as B solvent. As a result of HPLC analysis, it was confirmed that elution appeared as one big peak at about 9 minute positions (see FIGS. 4a to 4l).

Example 3

Measurement of Activity of Brazzein Multiple Variant

Since brazzein is not a sugar but a protein, sweetness may not be measured using a saccharimeter. Consequently, the activity was measured using the human gustatory system. Since the threshold values of initially sensing sweetness are different per person, the activity was measured by comparing the concentrations of initially sensing sweetness between a sugar solution and a brazzein solution. The subjects were composed of 10 men and 10 women, who were trained in advance. First, the standard sugar solution was sequentially tasted, and the concentration of initially sensing sweetness was checked. Brazzein was dissolved in distilled water (10.0 mg/mL) and diluted to set the concentration to 1 to 20 ng/mL, and the sweetness of the solution was tasted and the concentration of sensing sweetness as the threshold value was checked to measure the relative activity of sweetness among sugar, wild-type brazzein, and a brazzein variant. Specifically, the activity was measured as follows. Before the activity was measured, the subject was informed in advance of the test date and time to sense the taste in tiptop conditions, and was prohibited from drinking alcohol the day before the test date and eating food immediately before the test. The subject washed the palate with bottled water prepared, and then a sample according to the concentration of each kind was tasted in each of an amount of 100 μl sequentially from a low concentration to a high concentration. The resulting data were obtained by discarding dubious values through the Q test, minimizing the standard deviation, and calculating the average.

K4D_H30R_E35D_E40A, K4E_H30R_E35D_E40A, K4R_H30R_E35D_E40A, K4D_H30R_E35D_E40K, K4E_H30R_E35D_E40K, K4R_H30R_E35D_E40K, K4D_H30R_E35D_E40D, K4E_H30R_E35D_E40D, K4R_H30R_E35D_E40D, K4D_H30R_E35D_E40R, K4E_H30R_E35D_E40R, and K4R_H30R_E35D_E40R, which are brazzein multiple variants mutatedin order to increase the sweetening effects based on the tertiary variant, were 2,000,000 times, 2,000,000 times, 2,900,000 times, 1,500,000 times, 1,700,000 times, 2,000,000 times, 1,300,000 times, 1,250,000 times, 1,700,000 times, 1,800,000 times, 1,800,000 times, and 2,000,000 times, respectively, as sweet as sucrose in the same mass (see Table 3). Table 3 showed the relative activity of the variant compared to the activity (100%) of the wild-type brazzein. K4D_H30R_E35D_E40A, K4E_H30R_E35D_E40A, K4R_H30R_E35D_E40A, K4D_H30R_E35D_E40K, K4E_H30R_E35D_E40K, K4R_H30R_E35D_E40K, K4D_H30R_E35D_E40D, K4E_H30R_E35D_E40D, K4R_H30R_E35D_E40D, K4D_H30R_E35D_E40R, K4E_H30R_E35D_E40R, K4R_H30R_E35D_E40R, which are the brazzein multiple variants of the present invention, were 2,500 times, 2,500 times, 3,570 times, 1,920 times, 2,080 times, 2,500 times, 1,670 times, 1,560 times, 2,080 times, 2,270 times, 2,270 times, and 2,500 times, respectively, as sweet as the wild-type brazzein in the same mass.

TABLE 3

| Name of Molecule | Molecular weight | Threshold value of sweetness experiment | | Level of sweetness compared to sucrose | |
| --- | --- | --- | --- | --- | --- |
| | | (g (100 mL)$^{-1}$) | μM | (g/g) | (molecular) |
| Sucrose | 342.3 | 2.0 | 58,000 | 1 | 1 |
| WT-Brazzein | 6501 | 0.0025 | 3.84556 | 800 | 15,082 |
| Brazzein (Met-) | 6370 | 0.0013720 | 2.15385 | 1,458 | 26,929 |
| K4D_H30R_E35D_E40A | 6304 | 0.0000010 | 0.00158 | 2,000,000 | 36708861 |
| K4E_H30R_E35D_E40A | 6318 | 0.0000010 | 0.00158 | 2,000,000 | 36708861 |
| K4R_H30R_E35D_E40A | 6345 | 0.0000007 | 0.00110 | 2,857,143 | 52727273 |
| K4D_H30R_E35D_E40K | 6361 | 0.0000013 | 0.00204 | 1,598,481 | 28379848 |
| K4E_H30R_E35D_E40K | 6375 | 0.0000012 | 0.00188 | 1,666,666 | 30812500 |
| K4R_H30R_E35D_E40K | 6402 | 0.0000010 | 0.00156 | 2,000,000 | 37131600 |
| K4D_H30R_E35D_E40D | 6348 | 0.0000015 | 0.00236 | 1,333,333 | 24545600 |
| K4E_H30R_E35D_E40D | 6362 | 0.0000016 | 0.00251 | 1,250,000 | 23062250 |
| K4R_H30R_E35D_E40D | 6369 | 0.0000012 | 0.00188 | 1,666,666 | 30860187 |
| K4D_H30R_E35D_E40R | 6369 | 0.0000011 | 0.00172 | 1,818,181 | 33687455 |
| K4E_H30R_E35D_E40R | 6403 | 0.0000011 | 0.00172 | 1,818,181 | 33761273 |
| K4R_H30R_E35D_E40R | 6430 | 0.0000010 | 0.00156 | 2,000,000 | 37284000 |

Although the specific part of the present invention has been described in detail, it is obvious to the person skilled in the art that such a specific description is just a preferred embodiment and the scope of the present invention is not limited thereby. Consequently, the substantial scope of the present invention will be defined by the appended claims and equivalents thereof.

REFERENCE

Assadi-Porter, F. M., Aceti, D. J., and Markley, J. L. (2000). Arch. Biochem. Biophys., 376 (2), 259-265.

Assadi-Porter, F. M., Abildgaard, F., Blad, H., and Markley, J. L. (2003). The J. Biol. Chem., 278 (33), 31331-31339.

Assadi-Porter, F. M., Radek, J. T., Maillet, E. L., Quijada J., and Max, M. (2010). J. Mol. Biol., 398, 584-599.

Assadi-Porter, F. M., Tonelli, M., Maillet, E. M., Markley, J. L., and Max, M. (2010). Biochim Biophys Acta,. 1798 (2), 82-86.

Bopp, B. A., Price, P., Abbott, L., and Abbott, P. (1991). Food Sci. Tech,. 48, 71-95.

Butchko, H. H., et al., (2002). Aspartame: Review of Safety. Regul. Toxicol. Pharm., 35, S1-S93.

Caldwell, J. E., Abildgaard, F., Dzakula, Z., Ming, D., Hellenkant, G., and Markley, J. L. (1998). Nat. Struct. Biol., 5 (6), 427-431.

Do, H. D., Jo, H. J., Jo, D. H., and Kong, K. H. (2011). Bull. Korean Chem. Soc., 32 (11), 4106-4108.

Dixon, L. B., Pellizzon, M. A., Jawad, A. F., and Tershakovec, A. M. (2005). Obesity Research, 13 (10), 1727-1738.

Edens, L., Heslinga, L., Klok, R., Ledeboer, A.M., Maat, J., Toonen, M.Y., Visser C., and Verrips, C. T. (1982). Gene., 18, 112.

Gao, G. H., Dai, J. X., Ding, M., Hellekant, G., Wang, J. F., and Wang, D. C. (1999). Int. J. Biol. Macromol., 24, 351-359.

Hellekant, G., and Danilova V. (2005). Chem. Senses., 30, 88-89.

Hellekant, G., Danilova, V., Assadi-Porter, F. M., Aceti, D. J., Markley, J. L., and Jin, Z. (2003). FEBS Lett., 544, 33-37.

Jin, Z., Danilova, V., Assadi-Porter, F. M., Markley, J. L., and Hellekant, G. (2003). Chem. Senses, 28, 491-498.

Kaneko, R., and Kitabatake, N. (2001). Chem. Senses, 26, 167-177.

Kim, S. H., Kang, C. H., Kim, R., Cho, J. M., Lee, Y. B., and Lee, T. K. (1989). Protein Eng., 2, 571575.

Kitabatake, N., and Masuda, T. (2006). J. Biosci. Bioeng., 102 (5), 375-389.

Lee, J. J., Kong, J. N., Do, H. D., Jo, D. H., and Kong, K. H. (2010). Bull. Korean Chem. Soc., 31 (12), 3830-3833.

Liu, X., Maeda, S., Hu. Z., Aiuchi, T., Nakaya, K., and Kurihara, Y. (1993). Eur. J. Biochem., 67, 281-287.

Magnuson, B. A., Burdock. G. A., and Doull, J. (2007). Critical Reviews in Toxicology, 37 (8), 629-727.

Mauricio, B. (2003). Sugar chemistry: Quimica Nova., 26 (6), 906-912.

Ming, D., and Hellekant, G. (1994). FEBS Lett., 355, 106-108.

Moris, J. A., and Cagan, R. H. (1972). Biochim. Biophys. Acta, 261, 114-122.

Nelson, G., Hoon, M. A., Chandrashekar, J., Zhang, Y., Ryba, N. J., and Zuker, C. S. (2001). Cell., 106, 381-390.

Nirasawa, S., Nishino, T., Katahira, M., Uesugi, S., Hu, Z., and Kurihara, Y. (1994). Eur. J. Biochem., 223 (3), 989-995.

Packard, V. S. (1976). Processed Foods and The Consumer: Additives, Labeling, Standards, and Nutrition. Minneapolis. University of Minnesota Press., 332.

Paul M. P., and George B. K. (1980). Making Government Policy under Conditions of Scientific Uncertainty: a Century of Controversy about Saccharin in Congress and the Laboratory. Minerva, 18, 556-574.

Schagger, H., and von Jagow, G. (1987). Anal. Biochem., 166, 368-379.

Sung, Y. H., Shin, J., Chang, H. J., Cho, J. M., and Lee, W. T. (2001). J. Biol. Chem., 276 (22), 19624-19630.

Suzuki, M., Kurimoto, E., Nirasawa, S,. Masuda, Y., Hori, K., Kurihara, Y., Shimba, N., Kawai, M., Suzuki, E., and Kato, K. (2004). FEBS letters, 573 (13), 135-138.

Tancredi, T., Pastore, A., Salvadori, S., Esposito, V., and Temussi, P. A. (2004). Eur. J. Biochem., 271, 2231-2240.

Temussi, P. A. (2002). FEBS Lett., 526, 1-4.

Teodorico, T., Annalisa, P., Severo, S., Veronica, E., and Peiro, A. T. (2004). Eur. J. Biochem., 271, 2231-2240.

Theerasilp, S., and Kurihara, Y. (1988). J. Biol. Chem., 263, 11536-11539.

van der Wel, H., and Loeve, K. (1972). Benth. Eur. J. Biochem., 31, 221-225.

van der Wel. H., Larson, G., Hladik, A., Hellekant, G., and Glaser, D. (1989). Chem. Senses., 14, 75-79.

Walters, D. E., and Hellekant G. (2006). J. Agric. Food Chem., 54 (26), 10129-10133.

Walters, D. E., Cragin, T., Jin, Z., Rumbley, J. N., and Hellekant, G. (2009). Chem Senses., 34 (8), 679-683.

Wolf, M. G. (1922). J. Assoc. Off. Agricul. Chem., 6, 14-15.

Yamashita, H., Theerasilp, S., Aiuchi, T., Nakayama, K., Nakayama. Y., and Kurihara, Y. (1990). J. Biol. Chem., 265, 15770-15775.

Yoon, S. Y., Kong, J. N., Jo, D. H., and Kong, K. H. (2011). J. Foodchem., 129, 1327-1330.

What is claimed is:

1. A brazzein multiple variant having any one amino acid sequence selected from the group consisting of SEQ ID NOS. 11 to 22.

2. A nucleic acid molecule encoding the brazzein multiple variant of claim 1.

3. A recombinant vector comprising:
   (i) a promoter; and
   (ii) the nucleic acid molecule of claim 2 operatively linked with the promoter.

4. Host cells, in culture, that have been transformed with the recombinant vector of claim 3.

5. A method for making a brazzein multiple variant, the method comprising the following steps: (a) culturing the host cells of claim 4; and (b) separating a brazzein multiple variant protein from the cultured host cells.

6. A food composition for increasing a sugar content, which comprises the brazzein multiple variant of claim 1 as an active ingredient.

* * * * *

SEQUENCE LISTING

```
<160> NUMBER OF SEQ ID NOS: 35

<210> SEQ ID NO 1
<211> LENGTH: 53
<212> TYPE: PRT
<213> ORGANISM: Artificial Sequence
<220> FEATURE:
<223> OTHER INFORMATION: Brazzein Variant

<400> SEQUENCE: 1

Asp Lys Cys Lys Lys Val Tyr Glu Asn Tyr Pro Val Ser Lys Cys Gln
```

```
               1               5                  10                 15
Leu Ala Asn Gln Cys Asn Tyr Asp Cys Lys Leu Ala Lys Arg Ala Arg
                20                   25                 30

Ser Gly Asp Cys Phe Tyr Asp Lys Lys Arg Asn Leu Gln Cys Ile Cys
            35                 40                 45

Asp Tyr Cys Glu Tyr
        50

<210> SEQ ID NO 2
<211> LENGTH: 53
<212> TYPE: PRT
<213> ORGANISM: Artificial Sequence
<220> FEATURE:
<223> OTHER INFORMATION: Brazzein Variant

<400> SEQUENCE: 2

Asp Lys Cys Lys Lys Val Tyr Glu Asn Tyr Pro Val Ser Lys Cys Gln
1               5                  10                 15

Leu Ala Asn Gln Cys Asn Tyr Asp Cys Lys Leu Ala Lys Arg Ala Arg
                20                   25                 30

Ser Gly Asp Cys Phe Tyr Asp Ala Lys Arg Asn Leu Gln Cys Ile Cys
            35                 40                 45

Asp Tyr Cys Glu Tyr
        50

<210> SEQ ID NO 3
<211> LENGTH: 53
<212> TYPE: PRT
<213> ORGANISM: Artificial Sequence
<220> FEATURE:
<223> OTHER INFORMATION: Brazzein Variant

<400> SEQUENCE: 3

Asp Lys Cys Lys Lys Val Tyr Glu Asn Tyr Pro Val Ser Lys Cys Gln
1               5                  10                 15

Leu Ala Asn Gln Cys Asn Tyr Asp Cys Lys Leu Ala Lys Arg Ala Arg
                20                   25                 30

Ser Gly Asp Cys Phe Tyr Asp Asp Lys Arg Asn Leu Gln Cys Ile Cys
            35                 40                 45

Asp Tyr Cys Glu Tyr
        50

<210> SEQ ID NO 4
<211> LENGTH: 53
<212> TYPE: PRT
<213> ORGANISM: Artificial Sequence
<220> FEATURE:
<223> OTHER INFORMATION: Brazzein Variant

<400> SEQUENCE: 4

Asp Lys Cys Lys Lys Val Tyr Glu Asn Tyr Pro Val Ser Lys Cys Gln
1               5                  10                 15

Leu Ala Asn Gln Cys Asn Tyr Asp Cys Lys Leu Ala Lys Arg Ala Arg
                20                   25                 30

Ser Gly Asp Cys Phe Tyr Asp Arg Lys Arg Asn Leu Gln Cys Ile Cys
            35                 40                 45

Asp Tyr Cys Glu Tyr
        50

<210> SEQ ID NO 5
```

```
<211> LENGTH: 30
<212> TYPE: DNA
<213> ORGANISM: Artificial Sequence
<220> FEATURE:
<223> OTHER INFORMATION: PCR primer

<400> SEQUENCE: 5
gacaaatgcg ataaagttta cgaaaattac                                   30

<210> SEQ ID NO 6
<211> LENGTH: 30
<212> TYPE: DNA
<213> ORGANISM: Artificial Sequence
<220> FEATURE:
<223> OTHER INFORMATION: PCR primer

<400> SEQUENCE: 6
gtaattttcg taaactttat cgcatttgtc                                   30

<210> SEQ ID NO 7
<211> LENGTH: 30
<212> TYPE: DNA
<213> ORGANISM: Artificial Sequence
<220> FEATURE:
<223> OTHER INFORMATION: PCR primer

<400> SEQUENCE: 7
gacaaatgcg aaaagttta cgaaaattac                                    30

<210> SEQ ID NO 8
<211> LENGTH: 30
<212> TYPE: DNA
<213> ORGANISM: Artificial Sequence
<220> FEATURE:
<223> OTHER INFORMATION: PCR primer

<400> SEQUENCE: 8
gtaattttcg taaacttttt cgcatttgtc                                   30

<210> SEQ ID NO 9
<211> LENGTH: 24
<212> TYPE: DNA
<213> ORGANISM: Artificial Sequence
<220> FEATURE:
<223> OTHER INFORMATION: PCR primer

<400> SEQUENCE: 9
gacaaatgcc gcaaagttta cgaa                                         24

<210> SEQ ID NO 10
<211> LENGTH: 24
<212> TYPE: DNA
<213> ORGANISM: Artificial Sequence
<220> FEATURE:
<223> OTHER INFORMATION: PCR primer

<400> SEQUENCE: 10
ttcgtaaact ttgcggcatt tgtc                                         24

<210> SEQ ID NO 11
<211> LENGTH: 53
<212> TYPE: PRT
<213> ORGANISM: Artificial Sequence
<220> FEATURE:
<223> OTHER INFORMATION: Brazzein Variant

<400> SEQUENCE: 11
```

```
Asp Lys Cys Asp Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Lys Lys Arg Asn Leu Gln Cys Ile Cys
        35                  40                  45

Asp Tyr Cys Glu Tyr
        50

<210> SEQ ID NO 12
<211> LENGTH: 53
<212> TYPE: PRT
<213> ORGANISM: Artificial Sequence
<220> FEATURE:
<223> OTHER INFORMATION: Brazzein Variant

<400> SEQUENCE: 12

Asp Lys Cys Glu Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Lys Lys Arg Asn Leu Gln Cys Ile Cys
        35                  40                  45

Asp Tyr Cys Glu Tyr
        50

<210> SEQ ID NO 13
<211> LENGTH: 53
<212> TYPE: PRT
<213> ORGANISM: Artificial Sequence
<220> FEATURE:
<223> OTHER INFORMATION: Brazzein Variant

<400> SEQUENCE: 13

Asp Lys Cys Arg Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Lys Lys Arg Asn Leu Gln Cys Ile Cys
        35                  40                  45

Asp Tyr Cys Glu Tyr
        50

<210> SEQ ID NO 14
<211> LENGTH: 53
<212> TYPE: PRT
<213> ORGANISM: Artificial Sequence
<220> FEATURE:
<223> OTHER INFORMATION: Brazzein Variant

<400> SEQUENCE: 14

Asp Lys Cys Asp Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Ala Lys Arg Asn Leu Gln Cys Ile Cys
        35                  40                  45

Asp Tyr Cys Glu Tyr
        50
```

```
<210> SEQ ID NO 15
<211> LENGTH: 53
<212> TYPE: PRT
<213> ORGANISM: Artificial Sequence
<220> FEATURE:
<223> OTHER INFORMATION: Brazzein Variant

<400> SEQUENCE: 15

Asp Lys Cys Glu Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Ala Lys Arg Asn Leu Gln Cys Ile Cys
        35                  40                  45

Asp Tyr Cys Glu Tyr
    50

<210> SEQ ID NO 16
<211> LENGTH: 53
<212> TYPE: PRT
<213> ORGANISM: Artificial Sequence
<220> FEATURE:
<223> OTHER INFORMATION: Brazzein Variant

<400> SEQUENCE: 16

Asp Lys Cys Arg Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Ala Lys Arg Asn Leu Gln Cys Ile Cys
        35                  40                  45

Asp Tyr Cys Glu Tyr
    50

<210> SEQ ID NO 17
<211> LENGTH: 53
<212> TYPE: PRT
<213> ORGANISM: Artificial Sequence
<220> FEATURE:
<223> OTHER INFORMATION: Brazzein Variant

<400> SEQUENCE: 17

Asp Lys Cys Asp Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Asp Lys Arg Asn Leu Gln Cys Ile Cys
        35                  40                  45

Asp Tyr Cys Glu Tyr
    50

<210> SEQ ID NO 18
<211> LENGTH: 53
<212> TYPE: PRT
<213> ORGANISM: Artificial Sequence
<220> FEATURE:
<223> OTHER INFORMATION: Brazzein Variant

<400> SEQUENCE: 18

Asp Lys Cys Glu Lys Val Tyr Glu Asn Tyr Pro Val Ser Lys Cys Gln
1               5                   10                  15
```

```
Leu Ala Asn Gln Cys Asn Tyr Asp Cys Lys Leu Ala Lys Arg Ala Arg
            20                  25                  30

Ser Gly Asp Cys Phe Tyr Asp Ala Lys Arg Asn Leu Gln Cys Ile Cys
        35                  40                  45

Asp Tyr Cys Glu Tyr
        50

<210> SEQ ID NO 19
<211> LENGTH: 53
<212> TYPE: PRT
<213> ORGANISM: Artificial Sequence
<220> FEATURE:
<223> OTHER INFORMATION: Brazzein Variant

<400> SEQUENCE: 19

Asp Lys Cys Arg Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Lys Arg Asn Leu Gln Cys Ile Cys
        35                  40                  45

Asp Tyr Cys Glu Tyr
        50

<210> SEQ ID NO 20
<211> LENGTH: 53
<212> TYPE: PRT
<213> ORGANISM: Artificial Sequence
<220> FEATURE:
<223> OTHER INFORMATION: Brazzein Variant

<400> SEQUENCE: 20

Asp Lys Cys Asp Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Arg Lys Arg Asn Leu Gln Cys Ile Cys
        35                  40                  45

Asp Tyr Cys Glu Tyr
        50

<210> SEQ ID NO 21
<211> LENGTH: 53
<212> TYPE: PRT
<213> ORGANISM: Artificial Sequence
<220> FEATURE:
<223> OTHER INFORMATION: Brazzein Variant

<400> SEQUENCE: 21

Asp Lys Cys Glu Lys Val Tyr Glu Asn Tyr Pro Val Ser Lys Cys Gln
1               5                   10                  15

Leu Ala Asn Gln Cys Asn Tyr Asp Cys Lys Leu Ala Lys Arg Ala Arg
            20                  25                  30

Ser Gly Asp Cys Phe Tyr Asp Arg Lys Arg Asn Leu Gln Cys Ile Cys
        35                  40                  45

Asp Tyr Cys Glu Tyr
        50

<210> SEQ ID NO 22
<211> LENGTH: 53
<212> TYPE: PRT
```

<213> ORGANISM: Artificial Sequence
<220> FEATURE:
<223> OTHER INFORMATION: Brazzein Variant

<400> SEQUENCE: 22

Asp Lys Cys Arg Lys Val Tyr Glu Asn Tyr Pro Val Ser Lys Cys Gln
1 5 10 15

Leu Ala Asn Gln Cys Asn Tyr Asp Cys Lys Leu Ala Lys Arg Ala Arg
20 25 30

Ser Gly Asp Cys Phe Tyr Asp Arg Lys Arg Asn Leu Gln Cys Ile Cys
35 40 45

Asp Tyr Cys Glu Tyr
50

<210> SEQ ID NO 23
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 23
atggccgata agtgcgataa ggtttacgaa aattacccag tttctaagtg ccaacttgct 60
aatcaatgca attacgattg caagcttgct aagcgtgcta gatctggaga ttgcttttac 120
gataaaaaga gaaatcttca atgcatttgc gattactgcg aatactaa 168

<210> SEQ ID NO 24
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 24
atggccgata agtgcgaaaa ggtttacgaa aattacccag tttctaagtg ccaacttgct 60
aatcaatgca attacgattg caagcttgct aagcgtgcta gatctggaga ttgcttttac 120
gataaaaaga gaaatcttca atgcatttgc gattactgcg aatactaa 168

<210> SEQ ID NO 25
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 25
atggccgata agtgccgcaa ggtttacgaa aattacccag tttctaagtg ccaacttgct 60
aatcaatgca attacgattg caagcttgct aagcgtgcta gatctggaga ttgcttttac 120
gataaaaaga gaaatcttca atgcatttgc gattactgcg aatactaa 168

<210> SEQ ID NO 26
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 26
atggccgata agtgcgataa ggtttacgaa aattacccag tttctaagtg ccaacttgct 60
aatcaatgca attacgattg caagcttgct aagcgtgcta gatctggaga ttgcttttac 120
gatgccaaga gaaatcttca atgcatttgc gattactgcg aatactaa         168

<210> SEQ ID NO 27
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 27
atggccgata agtgcgaaaa ggtttacgaa aattacccag tttctaagtg ccaacttgct    60
aatcaatgca attacgattg caagcttgct aagcgtgcta gatctggaga ttgcttttac   120
gatgccaaga gaaatcttca atgcatttgc gattactgcg aatactaa                168

<210> SEQ ID NO 28
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 28
atggccgata agtgccgcaa ggtttacgaa aattacccag tttctaagtg ccaacttgct    60
aatcaatgca attacgattg caagcttgct aagcgtgcta gatctggaga ttgcttttac   120
gatgccaaga gaaatcttca atgcatttgc gattactgcg aatactaa                168

<210> SEQ ID NO 29
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 29
atggccgata agtgcgataa ggtttacgaa aattacccag tttctaagtg ccaacttgct    60
aatcaatgca attacgattg caagcttgct aagcgtgcta gatctggaga ttgcttttac   120
gatgacaaga gaaatcttca atgcatttgc gattactgcg aatactaa                168

<210> SEQ ID NO 30
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 30
atggccgata agtgcgaaaa ggtttacgaa aattacccag tttctaagtg ccaacttgct    60
aatcaatgca attacgattg caagcttgct aagcgtgcta gatctggaga ttgcttttac   120
gatgacaaga gaaatcttca atgcatttgc gattactgcg aatactaa                168

<210> SEQ ID NO 31
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 31
atggccgata agtgccgcaa ggtttacgaa aattacccag tttctaagtg ccaacttgct    60

```
aatcaatgca attacgattg caagcttgct aagcgtgcta gatctggaga ttgcttttac    120
gatgacaaga gaaatcttca atgcatttgc gattactgcg aatactaa                 168

<210> SEQ ID NO 32
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 32
atggccgata agtgcgataa ggtttacgaa aattacccag tttctaagtg ccaacttgct    60
aatcaatgca attacgattg caagcttgct aagcgtgcta gatctggaga ttgcttttac    120
gatcgtaaga gaaatcttca atgcatttgc gattactgcg aatactaa                 168

<210> SEQ ID NO 33
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 33
atggccgata agtgcgaaaa ggtttacgaa aattacccag tttctaagtg ccaacttgct    60
aatcaatgca attacgattg caagcttgct aagcgtgcta gatctggaga ttgcttttac    120
gatcgtaaga gaaatcttca atgcatttgc gattactgcg aatactaa                 168

<210> SEQ ID NO 34
<211> LENGTH: 168
<212> TYPE: DNA
<213> ORGANISM: Artificial Sequence
<220> FEATURE:
<223> OTHER INFORMATION: Brazzein Variant Coding Nucleotide Sequence

<400> SEQUENCE: 34
atggccgata agtgccgcaa ggtttacgaa aattacccag tttctaagtg ccaacttgct    60
aatcaatgca attacgattg caagcttgct aagcgtgcta gatctggaga ttgcttttac    120
gatcgtaaga gaaatcttca atgcatttgc gattactgcg aatactaa                 168

<210> SEQ ID NO 35
<211> LENGTH: 60
<212> TYPE: DNA
<213> ORGANISM: Escherichia coli

<400> SEQUENCE: 35
atgaaatacc tgctgccgac cgctgctgct ggtctgctgc tcctcgctgc ccagccggcg    60
```